United States Patent
Colton et al.

(10) Patent No.: US 8,993,833 B2
(45) Date of Patent: Mar. 31, 2015

(54) MODEL OF ALZHEIMER'S DISEASE

(75) Inventors: Carol Anne Colton, Cary, NC (US);
Michael Peter Vitek, Cary, NC (US);
Judianne Davis, East Setauket, NY (US); William E. VanNostrand, East Setauket, NY (US)

(73) Assignee: Duke University, Durham, NC (US)

( * ) Notice: Subject to any disclaimer, the term of this patent is extended or adjusted under 35 U.S.C. 154(b) by 1018 days.

(21) Appl. No.: 12/228,611

(22) Filed: Aug. 14, 2008

(65) Prior Publication Data

US 2009/0081128 A1 Mar. 26, 2009

Related U.S. Application Data

(60) Provisional application No. 60/964,647, filed on Aug. 14, 2007.

(51) Int. Cl.
| | | |
|---|---|---|
| *A01K 67/00* | (2006.01) | |
| *G01N 33/00* | (2006.01) | |
| *A01K 67/027* | (2006.01) | |
| *A61K 49/00* | (2006.01) | |
| *C12N 15/85* | (2006.01) | |

(52) U.S. Cl.
CPC ......... *A01K 67/0275* (2013.01); *A01K 67/0276* (2013.01); *A01K 2217/054* (2013.01); *A01K 2217/075* (2013.01); *A01K 2217/15* (2013.01); *A01K 2227/105* (2013.01); *A01K 2267/0312* (2013.01); *A61K 49/0008* (2013.01); *C12N 15/8509* (2013.01)
USPC ............ 800/12; 800/3; 800/8; 800/9; 800/13; 800/18

(58) Field of Classification Search
USPC .................................. 800/3, 8, 12
See application file for complete search history.

(56) References Cited

U.S. PATENT DOCUMENTS 7,663,018 B2   2/2010  Sommer et al.

OTHER PUBLICATIONS

Colton et al. PNAS 2006;103:12867-72, Published online Aug. 14, 2006.*
Nathan et al. J Exp Med 2005;202:1163-9.*
Ishii et al. FASEB J 2000;14:1485-9.*
Chishti et al. J Biol Chem 2001;276:21562-70.*
Pearson, Nature 2002;415:8-9.*
Simerly et al, Science 2003;300:297.*
Polejaeva et al. Nature 2000;407:86.*
Yanagimachi. Mol Cell Endocrinol 2002;187:241-8.*
Mullins et al. J Clin Invest Apr. 1996;97:1557-60.*
Moreadith et al, J. Mol. Med., Mar. 1997;75(3):208-16.*
Pera et al, Journal of Cell Science 2000;113: 5-10.*
Wall et al. J Dairy Sci 1997;80:2213-24.*
JAX Lab, mouse datasheet for APPSwDI, printed on Nov. 2011.*
Porzig et al. Biochem Biophy Res Comm 2007;358:644-9, online pub. date May 7, 2007.*
Bilkei-Gorzo et al. Pharmacol Ther 2014;142:244-57.*
Colton et al. J Alzheimers Dis. 2008; 15:571-87.*
Gherardini et al. Cell Mol Life Sci 2014;71:1-20.*
Boucher et al. J Clin Invest Feb. 1999; 103:441-5.*
Miller et al., 1995, FASEB J., vol. 9, pp. 190-199.*
Deonarain, 1998, Expert Opin. Ther. Pat., vol. 8, pp. 53-69.*
Cho et al. (2005) Obligatory role of inducible nitric oxide synthase in ischemic preconditioning. J. Cereb. Blood Flow Metab. 25: 493-501.
Davis et al. (2004). Early-onset and robust cerebral microvascular accumulation of amyloid beta-protein in transgenic mice expressing low levels of a vasculotropic Dutch/Iowa mutant form of amyloid beta-protein precursor. J. Biol. Chem. 279(19): 20296-20306.
Gamblin et al. (2003) Caspase cleavage of tau: linking amyloid and neurofibrillary tangles in Alzheimer's disease. Proc. Natl. Acad. Sci. USA. 100:10032-10037.
Hsiao et al. (1996). Correlative memory deficits, Aβ elevation, and amyloid plaques in transgenic mice. Science. 274:99-102.
Laubach et al. (1995) Mice Lacking inducible nitric oxide synthase are not resistant to lipopolysaccharide-induced death. Proc. Natl. Acad. Sci. USA. 92(23):10688-10692.
Lewis et al.(2000). Neurofibrillary tangles, amyotrophy and progressive motor disturbance in mice expressing mutant (P301L) tau protein. Nat. Genet. 25:402-405.
Lewis et al.(2000). Neurofibrillary tangles, amyotrophy and progressive motor disturbance in mice expressing mutant (P301L) tau protein. Erratum. Nat. Genet. 26:129.

* cited by examiner

*Primary Examiner* — Janice Li
(74) *Attorney, Agent, or Firm* — Jenkins, Wilson, Taylor & Hunt, P.A.

(57) ABSTRACT

A modified non-human warm-blooded vertebrate animal in which a biologically active human APP polypeptide is expressed, and in which function of its inducible Nitric Oxide Synthase (iNOS) protein is reduced as compared to a non-modified animal, methods of making the animal, and methods of testing a candidate composition for activity in the treatment of Alzheimer's Disease using the animal.

14 Claims, 11 Drawing Sheets
(10 of 11 Drawing Sheet(s) Filed in Color)

SEQUENCE LISTING

<160> NUMBER OF SEQ ID NOS: 2

<210> SEQ ID NO 1
<211> LENGTH: 20
<212> TYPE: DNA
<213> ORGANISM: Mus musculus

<400> SEQUENCE: 1
gcatcccaag tacgagtggt                    20

<210> SEQ ID NO 2
<211> LENGTH: 24
<212> TYPE: DNA
<213> ORGANISM: Mus musculus

<400> SEQUENCE: 2
attctgccag atgtgggtct tcca               24

MODEL OF ALZHEIMER'S DISEASE

CROSS-REFERENCE TO RELATED APPLICATIONS

The presently disclosed subject matter claims the benefit of U.S. Provisional Patent Application Ser. No. 60/964,647; filed Aug. 14, 2007; the disclosure of which is incorporated herein by reference in its entirety.

GRANT STATEMENT

The invention was made with government support under grant numbers AG19740, AG19780, and NS36645 awarded by the National Institutes of Heath. The government has certain rights in the invention.

TECHNICAL FIELD

The presently disclosed subject matter relates, in general, to modified non-human animals, for instance, a modified mouse, and methods of employing such animals to test candidate compositions to determine if they have activity in the amelioration of Alzheimer's Disease.

SUMMARY

Disclosed herein in some embodiments are modified non-human warm-blooded vertebrate animals in which a biologically active human APP polypeptide is expressed, and in which function of its inducible Nitric Oxide Synthase (iNOS) protein is reduced as compared to a non-modified animal, methods of making the animals, and methods of testing a candidate composition for activity in the treatment of Alzheimer's Disease using the animals.

Accordingly, it is an object of the presently disclosed subject matter to provide a modified non-human warm-blooded vertebrate animal in which a biologically active human APP polypeptide is expressed, and in which function of its inducible Nitric Oxide Synthase (iNOS) protein is reduced as compared to a non-modified animal. This and other objects are achieved in whole or in part by the presently disclosed subject matter.

An object of the presently disclosed subject matter having been stated above, other objects will become evident as the description proceeds, when taken in connection with the accompanying Figures and Examples as best described below.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 1A is a plot showing two-day radial arm water maze task. Mice receive 15 trials a day and each block represents the average of three trials. ● symbol with a dashed line indicates data from the APPSwDI mice, ♦ symbol with a solid line indicates data from the APPSwDI/NOS2−/− mice. * indicates P<0.05 for the individual data points, ** indicates P<0.01 for the individual data points.

FIG. 1B is a plot of Barnes maze. Mice receive 2 trials a day for 5 days the two trials are averaged to give a single value for each day. ● symbol with a dashed line indicated data from the APPSwDI mice, ♦ symbol with a solid line indicates data from the APPSwDI/NOS2−/− mice. ** indicates P<0.01 for the individual data points.

FIG. 1C is a table showing Aβ ELISA from brain lysates ±standard errors. No significant differences were found for soluble and insoluble Aβ40 and Aβ42 between APPSwDI/NOS2−/− and APPSwDI mice.

FIGS. 2A-2F show NeuN immunocytochemistry in the APPSwDI (FIGS. 2A, 2C and 2E) and the APPSwDI/NOS2−/− mouse (FIGS. 2B, 2D and 2F). FIGS. 2A and 2B show the NeuN staining in the whole hippocampus, 40× magnification; scale bar=120 μm. FIGS. 2C and 2D show NeuN staining in the CA3 region and FIGS. 2E and 2F show NeuN staining in the subiculum. 100× magnification, scale bar=50 μm.

FIG. 2G is a bar graph showing the stereological quantification of NeuN staining in the hippocampus, CA3 and subiculum. * indicates P<0.05 compared to all other genotypes, ** indicates P<0.01 compared to all other genotypes.

FIGS. 2H-2M show neurodegenerative markers for APPSwDI (FIGS. 2H-2J) and APPSwDI/NOS2−/− mice (FIGS. 2K-2M). FIGS. 2H and 2K show FLUORO-JADE C™ staining, FIGS. 2I and 2L show cleaved caspase 3 staining and FIGS. 2J and 2M show TUNEL staining. All are 400× magnification, each scale bar: 12.5 μm.

FIGS. 3A and 3B show AT8 immunohistochemistry in the hippocampus of the APPSwDI mouse (FIG. 3A) and the APPSwDI/NOS2−/− mouse (FIG. 3B). Magnification=40×, scale bar=120 μm.

FIG. 3C is a bar graph showing quantification of percent area occupied by positive stain. * indicates P<0.05, ** indicates P<0.01 compared to the APPSwDI.

FIG. 3D is an image and bar graph showing the western blot for AT8 performed on brain protein lysates. Abbreviations: N2-NOS2−/−, AN2-APPSwDI/NOS2−/−, A APPSwDI, JNPL3-JNPL3 tau transgenic. Below the AT8 band is the same blot probed for GAPDH as a control for protein loading. Densitometry analysis was normalized to the GAPDH values and is shown below the western blot images.

FIGS. 3E-3G are double immunofluorescence images where neuron specific β-tubulin is shown in red (FIG. 3E), AT8 is shown in green (FIG. 3F) and a merged image shows yellow regions indicating colocalization of the two markers (FIG. 3G).

FIGS. 4A and 4B are high magnification images of the AT8 staining in the subiculum of the APPSwDI/NOS2−/− mouse. FIG. 4A magnification=200×, scale bar=25 μm. FIG. 4B magnification=400×, scale bar=12.5 μm. Arrow in FIG. 4B indicates a cell showing morphology of an interneuron.

FIGS. 4C-4H show tau staining in the APPSwDI mouse (FIGS. 4C-4E) and the APPSwDI/NOS2−/− mouse (FIGS. 4F-4H). FIGS. 4C and 4F show tau 5 staining, which labels total tau, FIGS. 4D and 4G show AT8 staining, which labels hyperphosphorylated tau and FIGS. 4E and 4H show thioflavine-S staining, which labels aggregated protein. All are 400× magnification, scale bars: 12.5 μm.

FIGS. 4I and 4J show CD45 immunohistochemistry in the hippocampus of the APPSwDI (I) and the APPSwDI/NOS2−/− mouse (J). Magnification=40×, scale bar=120 µm.

FIG. 4K is a bar graph showing quantification of percent area occupied by positive stain for CD45. * indicates P<0.05, ** indicates P<0.01 compared to APPSwDI mice.

(FIGS. 6A-6C and 6F) CA4 hippocampal (FIG. 6A) and globus palladius (FIG. 6B) neurons from an APPsw/NOS2−/− mouse were immunopositive for tau phosphorylated at Ser-202/Thr-205 by using the CP13 antibody or the AT8 antibody in neurons from frontal cortex (FIG. 6C) or hippocampus (FIG. 6F). Note the dense hyperphosphorylated tau immunoreactivity in soma and apical dendrites in FIG. 6B. (FIGS. 6D and 6E) AT8 immunoreactivity was not observed in brain sections from littermate NOS2−/− mice (FIG. 6D; cortex) or APPsw mice (FIG. 6E; hippocampus). (FIG. 6G) Neurons from APPsw/NOS2−/− brain were also immunopositive for tau phosphorylated at Thr-231 by using the AT180 antibody in the cortex. (FIG. 6H) No AT180 staining was observed in littermate NOS2−/− brains. (FIG. 6I) AT180 immunoreactivity in cortical sections from a mouse expressing the P301L human tau mutation was used as a positive control for hyperphosphorylated tau.

(FIG. 7A) Total tau (Tau5+) levels are similar in APPsw/NOS2−/− brain compared with littermate NOS2−/− controls. (FIG. 7B) Western blot for AT8 immunoreactive bands in APPsw/NOS2−/−, Tau−/−, P301L human tau mutation, WT, and NOS2−/− mice.

(FIGS. 8A and 8B) Trapped aggregates from whole brain filtrates were immunoreactive to Tau5 (FIG. 8A) and AT8 (FIG. 8B). APPsw/Tau−/− or Tau−/− brains served as negative controls, and P301L mouse brain served as positive control for the presence of tau aggregates. AT8 did not cross-react with Aβ aggregates formed by the addition of preaggregated Aβ42 to brain lysates and then filtered. Filter-trapped Aβ aggregates were detected by 4G8, an antibody against Aβ peptide. (FIG. 8C) Aggregates (Tau5+) were also detected by using scanning EM. Tau5+ aggregates were observed in lysates from APPsw/NOS2−/−, P301L mice, and autopsied AD brain samples. (FIG. 8D) Intracellular tau aggregates were detected by using thioflavin S histochemistry. Fluorescent particles were observed in neuronal somas from APPsw/NOS2−/− brains, but not littermate controls.

(FIG. 9A) Amyloid deposits in brain sections from APPsw/NOS2−/− mice were detected by using thioflavin S staining and immunoreactivity to the 4G8 antibody (Inset). (FIGS. 9B-9D) Aβ levels in brain lysates of the APPsw/NOS2−/− mice were compared with APPsw littermate controls by using an ELISA. Average values (±SEM) for the ratio of Aβ40 to Aβ42 (FIG. 9D), soluble and insoluble Aβ levels (FIG. 9C), and total Aβ levels (FIG. 9B) are shown. ns, no significant difference.

(FIG. 10A) Degenerating neurons were observed in cortical sections from APPsw/NOS2−/− mouse brains. (FIGS. 10B and 10C) No degenerating neurons were observed with fluorojade B staining in brain sections from WT (FIG. 10B) or APPsw (FIG. 10C) brains. (FIG. 10D) Intense staining was observed in a head-injured APPsw control mouse brain.

(FIGS. 11A-11D) Cleaved caspase-3 immunoreactivity was increased in hippocampal neurons and their processes in the APPsw/NOS2−/− brain (FIG. 11A) compared with NOS2−/− (FIG. 11B), APPsw (FIG. 11C), and WT (FIG. 11D) control mice. (FIG. 11C) NOS2−/− mice demonstrated low, but clearly observable, cleaved caspase immunoreactivity, confirming published data demonstrating increased caspase-3 activity in the NOS2−/− mouse brain (Cho et al., (2005) J. Cereb. Blood Flow Metab. 25, 493-501; Zhou et al., (2005) J. Cereb. Blood Flow Metab. 25, 348-357). (FIGS. 11E and 11F) Neurons in the APPsw/NOS2−/− brain also demonstrated immunoreactivity for caspase-cleaved (truncated) tau by using the TauC3 antibody (FIG. 11E) compared with APPsw (FIG. 11F) brains.

DETAILED DESCRIPTION

Figure 1:
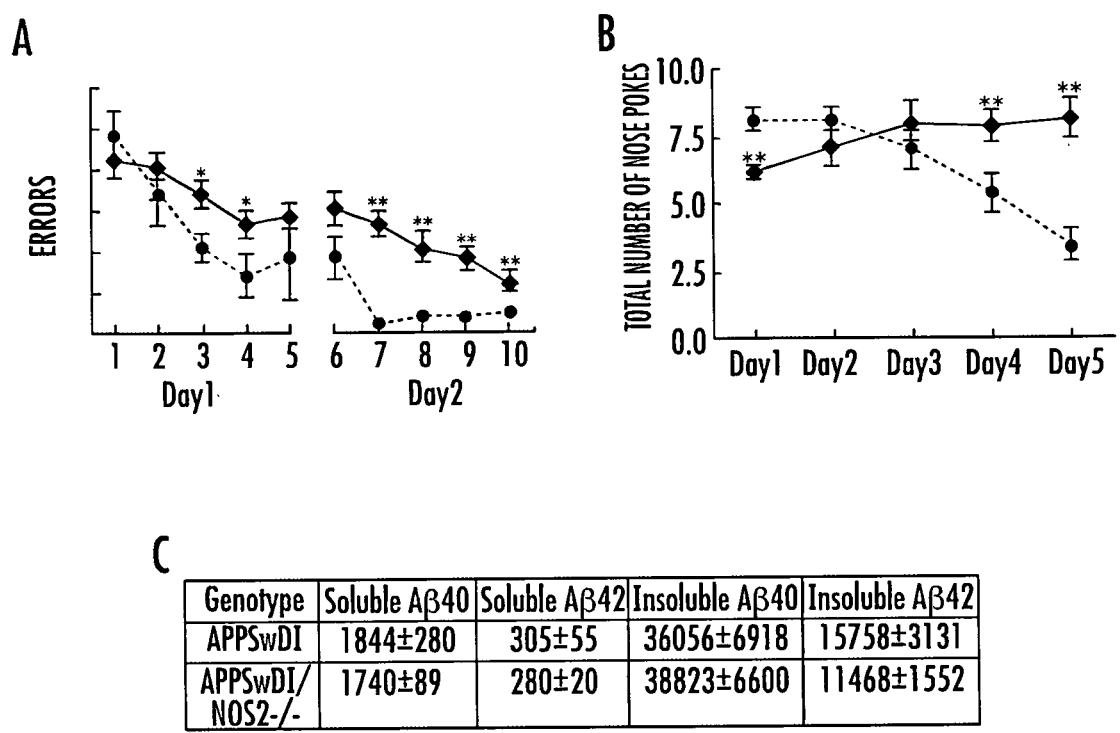
FIGS. 1A-1C depict that APPSwDI/NOS2−/− mice have significant spatial memory impairment compared to the APPSwDI mice with no significant difference in Aβ.

Disclosed herein is the production of the full spectrum of pathology and behavior that is associated with human Alzheimer's Disease in a modified non-human animal, such as a mouse. In some embodiments the presently disclosed subject matter provides for the expression of a human Amyloid Peptide Precursor (APP) protein in a transgenic mouse and the removal of expression and/or the removal of function of the mouse's inducible Nitric Oxide Synthase (iNOS) protein. Expression of a human APP protein is accomplished by use of transgenic technology to insert a cDNA or gene sequence into the genome of the mouse and that programs the synthesis of the human APP protein under control of an appropriate promoter sequence. Vectors, such as but not limited to lentiviral vectors, adenoviral vectors, and the like, that can program the expression of human APP protein are also acceptable. Removal of expression of the iNOS protein can be accomplished by genetically deleting the NOS2 gene that encodes the iNOS protein, also referred to herein as a NOS2 knockout or NOS2 null mouse. Alternatively, iNOS protein expression can be reduced with small interfering ribonucleic acids (siRNAs) that are well known to selectively reduce expression of a protein. As another alternative, arginine is the substrate for the iNOS enzyme and reduction of arginine levels through starvation for arginine and/or addition of non-hydrolyzable arginine analogs (also referred to herein as iNOS inhibitors) can reduce the ability of the iNOS enzyme to produce nitric oxide or NO.

As disclosed in the Examples, Tg2576 mice expressing the human Amyloid Peptide Precursor protein (APP) typically overexpress amyloid beta peptide, Abeta. These Abeta peptides aggregate in the brains of Tg2576 mice to form structures that resemble the amyloid plaques that are seen in patients with Alzheimer's disease. However, Tg2576 mice do not display the other two pathological hallmarks of AD which are: neurofibrillary tangles (NFTs) and neuronal death. Similarly, these Tg2576 mice do not display robust deficits in learning and memory performance on behavioral tests.

NOS2 knockout mice fail to display amyloid plaques and/or neurofibrillary tangles and do not show neuronal loss. In addition, NOS2 knockout mice do not display robust deficits in learning and memory performance on behavioral tests.

Mating of Tg2576 mice to NOS2 knockout mice yields a double transgenic mouse that expresses human APP protein and that does not express mouse iNOS protein. These APP/NOS2−/− double transgenic mice display amyloid plaques, neurofibrillary tangles and show neuronal loss in their brains.

In accordance with the presently disclosed subject matter, SwDI-APP transgenic mice have been mated with NOS2 knockout mice. The resulting SwDI-APP/NOS2−/− double transgenic mice display robust amyloid plaque and neurofibrillary tangle pathologies. They also display cerebrovascular amyloid deposits. These SwDI-APP/NOS2−/− mice also display robust behavioral deficits in a Radial Arm Water Maze test of spatial learning and memory and in a Barnes Maze test of spatial learning and memory.

The success of both the Tg2576-APP/NOS2−/− and the SwDI-APP/NOS2−/− transgenic mice to display amyloid plaques, neurofibrillary tangles and neuronal loss provides the basis for an aspect of the presently disclosed subject matter that expression of human APP protein and removal of iNOS enzymatic activity are both required to generate neurofibrillary tangle pathology comprising endogenous mouse tau proteins. In addition, both amyloid plaque-like pathology and neurofibrillary tangle-like pathology play a role in the observed neuronal loss. When amyloid plaque-like pathology, neurofibrillary tangle-like pathology and neuronal loss are present, then behavioral deficits in learning and memory are also observed in these mice. Each of these pathologies and the functional deficits in behavior are well known to occur in Alzheimer's patients. Functional deficits in behavior form the clinical basis for diagnosing senile dementia of the Alzheimer's type. Post-mortem confirmation of the presence of Alzheimer's disease is assayed by the presence of increased numbers of amyloid plaques and of neurofibrillary tangles in the subject's brains. The presence of these pathologies is highly correlated with neuron loss in the brains of patients with Alzheimer's disease.

It must be noted that as used herein and in the appended claims, the singular forms "a", "and", and "the" include plural referents unless the context clearly dictates otherwise. Thus, for example, reference to "a construct" includes a plurality of such constructs and reference to "the nucleic acid" includes reference to one or more nucleic acids and to equivalents thereof known to those skilled in the art, and so forth.

Unless defined otherwise, all technical and scientific terms used herein have the same meaning as commonly understood to one of ordinary skill in the art to which the presently disclosed subject matter belongs. Although any methods, devices and materials similar or equivalent to those described herein can be used in the practice or testing of the presently disclosed subject matter, the preferred methods, devices and materials are now described.

All publications mentioned herein are incorporated herein by reference for the purpose of describing and disclosing, for example, the constructs, and methodologies that are described in the publications, which might be used in connection with the presently disclosed subject matter. The publications discussed above and throughout the text are provided solely for their disclosure prior to the filing date of the present application. Nothing herein is to be construed as an admission that the inventors are not entitled to antedate such disclosure by virtue of prior disclosed subject matter.

I. Definitions

"Antibodies" refers to whole antibodies and antibody fragments or molecules including antibody fragments, including, but not limited to, single chain antibodies, humanized antibodies, and Fab, $F(ab')_2$, $V_h$, $V_l$, Fd, and single or double chain Fv fragments.

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

By "modified animal" is meant a non-human animal, usually a mammal (e.g., mouse, rat, rabbit, hamster, etc.), having its genome, protein function, or both, modified in some manner. For example, a modified animal can have a non-endogenous (i.e., heterologous) nucleic acid sequence present as an extrachromosomal element in a portion of its cells or stably integrated into its germ line DNA (i.e., in the genomic sequence of most or all of its cells). A heterologous nucleic acid is introduced into the germ line of such modified animals by genetic manipulation of, for example, embryos or embryonic stem cells of the host animal.

A "knock-out" of a gene means an alteration in the sequence of the gene that results in a decrease of function of the target gene, preferably such that target gene expression is undetectable or insignificant. A knock-out of an endogenous NOS2 gene means that function of the NOS2 gene has been substantially decreased so that expression is not detectable or only present at insignificant levels. "Knock-out" transgenics can be modified animals having a heterozygous knock-out of the NOS2 gene or a homozygous knock-out of the NOS2 gene. "Knock-outs" also include conditional knock-outs, where alteration of the target gene can occur upon, for example, exposure of the animal to a substance that promotes target gene alteration, introduction of an enzyme that promotes recombination at the target gene site (e.g., Cre in the Cre-lox system), or other method for directing the target gene alteration postnatally.

The terms "small interfering RNA", "short interfering RNA", and "siRNA" are used interchangeably and refer to any nucleic acid molecule capable of mediating RNA interference (RNAi) or gene silencing. See e.g., Bass, 2001; Elbashir et al., 2001a; and PCT International Publication Nos. WO 00/44895, WO 01/36646, WO 99/32619, WO 00/01846, WO 01/29058, WO 99/07409, and WO 00/44914.

The term "transgene" is used herein to describe genetic material that has been or is about to be artificially inserted into the genome of a warm-blooded vertebrate animal, particularly a cell of a living animal.

By "transformation" is meant a permanent or transient genetic change, preferably a permanent genetic change, induced in a cell following incorporation of new DNA (i.e., DNA exogenous to the cell). Where the cell is a mammalian cell, a permanent genetic change is generally achieved by introduction of the DNA into the genome of the cell.

By "construct" is meant a recombinant nucleic acid, generally recombinant DNA, which has been generated for the purpose of the expression of a specific nucleotide sequence(s), or is to be used in the construction of other recombinant nucleotide sequences.

By "operably linked" is meant that a DNA sequence and a regulatory sequence(s) are connected in such a way as to permit gene expression when the appropriate molecules (e.g., transcriptional activator proteins) are bound to the regulatory sequence(s).

By "operatively inserted" is meant that a nucleotide sequence of interest is positioned adjacent a nucleotide sequence that directs transcription and translation of the introduced nucleotide sequence of interest (i.e., facilitates the production of, e.g., a polypeptide encoded by an APP sequence).

The term "subject" as used herein refers to any invertebrate or vertebrate species. The methods of the presently disclosed subject matter are particularly useful in the treatment of warm-blooded vertebrates. Thus, in some embodiments, the presently disclosed concerns mammals and birds.

The term "about", as used herein when referring to a measurable value such as an amount of weight, time, dose, etc. is meant to encompass variations of ±20% or ±10%, more preferably ±5%, even more preferably ±1%, and still more preferably ±0.1% from the specified amount, as such variations are appropriate to perform the disclosed method.

II. Modified Non-Human Animals

Disclosed herein in some embodiments are modified non-human warm-blooded vertebrate animals in which a biologically active human APP polypeptide is expressed, and in which function of its inducible Nitric Oxide Synthase (iNOS) protein is reduced as compared to a non-modified animal and methods of making the animals.

The term "transgene" is used herein to describe genetic material that has been or is about to be artificially inserted into the genome of a mammalian cell, particularly a mammalian cell of a living animal. The transgene is used to transform a cell, meaning that a permanent or transient genetic change, optionally a permanent genetic change, is induced in a cell following incorporation of exogenous DNA. A permanent genetic change is generally achieved by introduction of the DNA into the genome of the cell.

Vectors for stable integration include plasmids, retroviruses and other animal viruses, bacterial artificial chromosomes (BACs), yeast artificial chromosomes (YACs), cosmids and the like. The term "vector", as used herein refers to a DNA molecule having sequences that enable its replication in a compatible host cell. A vector also includes nucleotide sequences to permit ligation of nucleotide sequences within the vector, wherein such nucleotide sequences are also replicated in a compatible host cell. A vector can also mediate recombinant production of an APP polypeptide, as described further herein below. Representative vectors include but are not limited to lentiviral vectors, adenoviral vectors, and the like.

Useful animals should be warm-blooded non-human vertebrates, for instance, mammals and birds. More particularly, the animal can be selected from the group consisting of rodent, swine, bird, ruminant, and primate. Even more particularly, the animal can be selected from the group consisting of a mouse, a rat, a pig, a guinea pig, poultry, an emu, an ostrich, a goat, a cow, a sheep, and a rabbit. Of interest are modified mammals, e.g. cows, pigs, goats, horses, etc., and particularly rodents, e.g. rats, mice, etc. In some embodiments, the transgenic animals are mice.

Modified animals can comprise an exogenous nucleic acid sequence present as an extrachromosomal element or stably integrated in all or a portion of its cells, especially in germ cells. In the context of a transgenic modified animal, unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

The exogenous gene is usually either from a different species than the animal host, or is otherwise altered in its coding or non-coding sequence. The introduced gene can be a wild-type gene, naturally occurring polymorphism, or a genetically manipulated sequence, for example having deletions, substitutions or insertions in the coding or non-coding regions. Where the introduced gene is a coding sequence, it is usually operably linked to a promoter, which can be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

In some embodiments, the presently disclosed modified animals comprise genetic alterations to provide for expression of a biologically active APP polypeptide, and/or expression of a desired biologically active APP sequence (e.g., human APP).

The transgenic animals of the presently disclosed subject matter can comprise other genetic alterations in addition to the presence of the APP-encoding sequence. For example, the host's genome can be altered to affect the function of endogenous genes (e.g., endogenous NOS2 gene), contain marker genes, or other genetic alterations consistent with the goals of the presently disclosed subject matter.

For example, the modified animals can be "knockouts" or "null" for a target gene(s) as is consistent with the goals of the presently disclosed subject matter. Knockouts have a partial or complete loss of function in one or both alleles of an endogenous gene of interest (e.g., NOS2).

In a knockout, it can be desirable for the target gene expression to be undetectable or insignificant. For example, a knockout of a NOS2 gene means that function of the NOS2 gene has been substantially decreased so that expression is not detectable or only present at insignificant levels. This can be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches can also be used to achieve the "knockout". A chromosomal deletion of all or part of the native gene can be induced, including deletions of the non-coding regions, particularly the promoter region, 3' regulatory sequences, enhancers, or deletions of gene that activate expression of NOS2 genes. A functional knock-out can also be achieved by the introduction of an anti-sense construct that blocks expression of the native genes (for example, see Li and Cohen (1996) Cell 85:319-329). "Knockouts" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

Alternatively or in addition, iNOS protein expression can be reduced with small interfering ribonucleic acids (siRNAs)

that are well known to selectively reduce expression of a protein. In some embodiments, the siRNA comprises a double stranded polynucleotide molecule comprising complementary sense and antisense regions, wherein the antisense region comprises a sequence complementary to a region of a target nucleic acid molecule (for example, an mRNA encoding NOS2). In some embodiments, the siRNA comprises a single stranded polynucleotide having self-complementary sense and antisense regions, wherein the antisense region comprises a sequence complementary to a region of a target nucleic acid molecule. In some embodiments, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

Alternatively or in addition, arginine is the substrate for the iNOS enzyme and reduction of arginine levels through starvation for arginine and/or addition of non-hydrolyzable arginine analogs (also referred to herein as iNOS inhibitors) can reduce the ability of the iNOS enzyme to produce nitric oxide or NO. Suitable iNOS inhibitors are known in the art and would be apparent to one of ordinary skill in the art upon a review of the instant disclosure.

III. Nucleic Acid Compositions

Constructs for use in the presently disclose subject matter include any construct suitable for use in the generation of modified animals having the desired levels of expression of a desired APP- and/or NOS2-encoding sequence. Methods for isolating and cloning a desired sequence, as well as suitable constructs for expression of a selected sequence in a host animal, are well known in the art. The construct can include sequences other than the desired APP- and/or NOS2-encoding sequences. For example, a detectable marker, such as lac Z can be included in the construct, where upregulation of expression of the encoded sequence will result in an easily detected change in phenotype.

The terms "APP gene" and "NOS2 gene" are used generically to refer to desired APP and NOS2 genes, e.g. homologs from rat, human, mouse, guinea pig, etc., and their alternate forms. A human APP gene is a representative APP gene. A mouse NOS2 gene is a representative NOS2 gene. The terms "APP gene" and "NOS2 gene" are also intended to mean the open reading frame encoding specific polypeptides, introns, and adjacent 5' and 3' non-coding nucleotide sequences involved in the regulation of expression, up to about 1 kb beyond the coding region, but possibly further in either direction. The DNA sequences encoding APP and NOS2 can be cDNA or genomic DNA or a fragment thereof. The genes can be introduced into an appropriate vector for extrachromosomal maintenance or for integration into the host.

The genomic sequences of particular interest comprise the nucleic acid present between the initiation codon and the stop codon, including all of the introns that are normally present in a native chromosome. They can further include the 3' and 5' untranslated regions found in the mature mRNA. They can further include specific transcriptional and translational regulatory sequences, such as promoters, enhancers, etc., including about 1 kb, but possibly more, of flanking genomic DNA at either the 5' or 3' end of the transcribed region. The genomic DNA can be isolated as a fragment of 100 kb or smaller; and substantially free of flanking chromosomal sequence.

The sequences of the 5' regions of the desired gene, and further 5' upstream sequences and 3' downstream sequences, can be utilized for promoter elements, including enhancer-binding sites, which provide for expression in suitable tissues.

The nucleic acid compositions used in the presently disclosed subject matter can encode all or a part of a gene or coding sequence as appropriate. Fragments can be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

Several isoforms and homologs of APP and NOS2 have been isolated and cloned. Additional homologs of cloned APP and NOS2 are identified by various methods known in the art. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity can be determined by hybridization under more stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes can be any species, e.g. primate, rodents, canines, felines, bovines, ovines, equines, etc.

Where desirable, the nucleic acid sequences, including flanking promoter regions and coding regions, can be mutated in various ways known in the art to generate targeted changes in the sequence of the encoded protein, splice variant production, etc. The sequence changes can be substitutions, insertions or deletions. Deletions can include large changes, such as deletions of a domain or exon. Other modifications of interest include epitope tagging, e.g. with the FLAG system, HA, etc. For studies of subcellular localization, fusion proteins with green fluorescent proteins (GFP) can be used. Such mutated genes can be used to study structure-function relationships, or to alter properties of the proteins that affect their function or regulation. The coding sequence can also be provided as a fusion protein. Methods for production of constructs are well known in the art (see, e.g., Wyss-Coray et al. (1995) *Am. J. Pathol.* 147:53-67).

Techniques for in vitro mutagenesis of cloned genes are known. Examples of protocols for scanning mutations can be found in Gustin et al., 1993 *Biotechniques* 14:22; Barany, 1985 *Gene* 37:111-23; Colicelli et al., 1985 *Mol Gen Genet.* 199:537-9; and Prentid et al., 1984 Gene 29:303-13. Methods for site specific mutagenesis can be found in Sambrook et al., 1989 *Molecular Cloning: A Laboratory Manual*, CSH Press, pp. 15.3-15.108; Weiner et al., 1993 Gene 126:35-41; Sayers et al., 1992 *Biotechniques* 13:592-6; Jones and Winistorfer, 1992 *Biotechniques* 12:528-30; Barton et al., 1990 *Nucleic Acids Res* 18:7349-55; Marotti and Tomich, 1989 *Gene Anal Tech* 6:67-70; and Zhu 1989 *Anal Biochem* 177:120-4.

In the case of APP, the host animals can be homozygous or heterozygous for the APP-encoding sequence, preferably homozygous. The APP gene can also be operably linked to a promoter to provide for a desired level of expression in the host animal and/or for tissue-specific expression. Expression of APP can be either constitute or inducible, typically constitutive.

In another aspect of the presently disclosed subject matter, siRNA molecules are expressed from transcription units inserted into nucleic acid vectors (alternatively referred to generally as "recombinant vectors" or "expression vectors"). The recombinant vectors can be, for example, DNA plasmids or viral vectors. Various expression vectors are known in the art. The selection of the appropriate expression vector can be made on the basis of several factors including, but not limited to the cell type wherein expression is desired. For example, mammalian expression vectors can be used to express the nucleic acids of the presently disclosed subject matter when the target cell is a mammalian cell.

Exemplary siRNA expressing viral vectors can be constructed based on lentivirus, adenovirus, adeno-associated virus, retrovirus, or alphavirus. The recombinant vectors capable of expressing the siRNA molecules can be delivered as described herein, and persist in target cells. Alternatively, viral vectors can be used that provide for transient expression of siRNA molecules.

Incorporation of a nucleic acid construct into a viral genome can be optionally performed by ligating the construct into an appropriate restriction site in the genome of the virus. Viral genomes can then be packaged into viral coats or capsids by any suitable procedure. In particular, any suitable packaging cell line can be used to generate viral vectors of the presently disclosed subject matter. These packaging lines complement the conditionally replication deficient viral genomes of the presently disclosed subject matter, as they include, typically incorporated into their genomes, the genes which have been put under an inducible promoter deleted in the conditionally replication competent vectors. Thus, the use of packaging lines allows viral vectors of the presently disclosed subject matter to be generated in culture.

IV. Methods of Making Modified Animals

It is thus within the scope of the presently disclosed subject matter to prepare a modified non-human animal that expresses an APP gene. In some embodiments the animal is a transgenic animal, and a representative transgenic animal is a transgenic mouse.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding an APP gene product are injected into fertilized mouse eggs. The injected eggs are implanted in pseudo pregnant females and are grown to term to provide transgenic mice whose cells express an APP gene product.

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection are included. Methods for generating cells having targeted gene modifications through homologous recombination are known in the art. For various techniques for transfecting mammalian cells, see Keown et al. (1990) *Methods in Enzymology* 185:527-537.

For embryonic stem (ES) cells, an ES cell line can be employed, or embryonic cells can be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they can be used to produce transgenic animals. After transformation, the cells are plated onto a feeder layer in an appropriate medium. Cells containing the construct can be detected by employing a selective medium. After sufficient time for colonies to grow, they are picked and analyzed for the occurrence of homologous recombination or integration of the construct. Those colonies that are positive can then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture.

A modified animal of the presently disclosed subject matter can also comprise a mouse with targeted modification of the NOS2 gene. Mice strains with complete or partial functional inactivation of the NOS2 gene in all somatic cells are generated using standard techniques of site-specific recombination in murine embryonic stem cells. See Capecchi (1989) *Science* 244(4910):1288-1292; Thomas & Capecchi (1990) *Nature* 346(6287):847-850.

Alternative approaches include the use of anti-sense or ribozyme NOS2 constructs, driven by a universal or tissue-specific promoter, to reduce levels of NOS2 in somatic cells, thus achieving a "knock-down" of individual isoforms (Luyckx et al. (1999) *Proc Natl Acad Sci USA* 96(21):12174-12179). The presently disclosed subject matter also provides the generation of murine strains with conditional or inducible inactivation of the NOS2 gene (Sauer (1998) *Methods* 14(4): 381-392; Ding et al. (1997) *J Biol Chem* 272(44):28142-28148).

In some embodiments the presently disclosed subject matter takes advantage of the ability of short, double stranded RNA molecules to cause the down regulation of cellular genes, i.e., NOS2, a process referred to as RNA interference. As used herein, "RNA interference" (RNAi) refers to a process of sequence-specific post-transcriptional gene silencing mediated by a small interfering RNA (siRNA). See generally Fire et al., 1998. The process of post-transcriptional gene silencing is thought to be an evolutionarily conserved cellular defense mechanism that has evolved to prevent the expression of foreign genes (Fire, 1999).

RNAi might have evolved to protect cells and organisms against the production of double stranded RNA (dsRNA) molecules resulting from infection by certain viruses (particularly the double stranded RNA viruses or those viruses for which the life cycle includes a double stranded RNA intermediate) or the random integration of transposon elements into the host genome via a mechanism that specifically degrades single stranded RNA or viral genomic RNA homologous to the double stranded RNA species.

The presence of dsRNA in cells triggers various responses, one of which is RNAi. RNAi appears to be different from the interferon response to dsRNA, which results from dsRNA-mediated activation of an RNA-dependent protein kinase (PKR) and 2',5'-oligoadenylate synthetase, resulting in non-specific cleavage of mRNA by ribonucleaset.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA) (Bernstein et al., 2001). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001b).

RNAi has been described in several cell type and organisms. Fire et al., 1998 described RNAi in *C. elegans*. Wianny & Zernicka-Goetz, 1999 disclose RNAi mediated by dsRNA in mouse embryos. Hammond et al., 2000 were able to induce RNAi in *Drosophila* cells by transfecting dsRNA into these cells. Elbashir et al. (2001a) demonstrated the presence of RNAi in cultured mammalian cells including human embryonic kidney and HeLa cells by the introduction of duplexes of synthetic 21 nucleotide RNAs.

Experiments using *Drosophila* embryonic lysates revealed certain aspects of siRNA length, structure, chemical composition, and sequence that are involved in RNAi activity. See Elbashir et al., 2001c. In this assay, 21 nucleotide siRNA duplexes were most active when they contain 3'-overhangs of two nucleotides. Also, the position of the cleavage site in the target RNA was shown to be defined by the 5'-end of the siRNA guide sequence rather than the 3'-end (Elbashir et al., 2001b).

Other studies have indicated that a 5'-phosphate on the target-complementary strand of a siRNA duplex is required for siRNA activity and that ATP is utilized to maintain the 5'-phosphate moiety on the siRNA (Nykanen et al., 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT

International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

Alternatively or in addition, arginine is the substrate for the iNOS enzyme and reduction of arginine levels through starvation for arginine and/or addition of non-hydrolyzable arginine analogs (also referred to herein as iNOS inhibitors) can reduce the ability of the iNOS enzyme to produce nitric oxide or NO. Suitable iNOS inhibitors are known in the art and would be apparent to one of ordinary skill in the art upon a review of the instant disclosure. Thus, the animal is maintained in a state of argininie starvation, through diet or other approach as would be apparent to one of ordinary skill in the art upon a review of the instant disclosure; and/or the animal is administered an iNOS inhibitor at a desired time.

V. Drug Screening Assays

A method of testing a candidate composition for activity in treating Alzheimer's Disease is also provided in accordance with the presently disclosed subject matter. A wide variety of tests and assays can be used for this purpose, e.g. determination of the localization of drugs after administration, immunoassays, and the like. Depending on the particular assay, whole animals can be used, or cells derived therefrom. Cells can be freshly isolated from an animal, or can be immortalized in culture.

In some embodiments, the methods comprise providing a modified non-human warm-blooded vertebrate animal in which a biologically active human APP polypeptide is expressed, and in which function of its inducible Nitric Oxide Synthase (iNOS) protein is reduced as compared to a non-modified animal; administering the candidate composition to the modified non-human animal; and observing the modified non-human animal for determination of an ameliorating change in the modified non-human animal indicative of activity in the treatment of Alzheimer's Disease. In some embodiments the observed change is a change in a pathology and/or a behavior that is associated with human Alzheimer's Disease that is present in the modified non-human animal.

A number of assays are known in the art for determining the effect of a drug on conditions and phenomena associated with Alzheimer's Disease. Some examples are provided herein, although it will be understood by one of skill in the art that many other assays and tests can also be used. The subject animals themselves are used, alone or in combination with control animals.

Thus, through use of the subject modified animals or cells derived therefrom, one can identify ligands or substrates that modulate a pathology and/or behavior that is associated with human Alzheimer's Disease. Of particular interest are screening assays for candidate compositions that have a low toxicity for human cells.

The term "candidate composition" as used herein describes any molecule, e.g. protein or pharmaceutical, with the capability of affecting the molecular and clinical phenomena associated with human Alzheimer's Disease. Generally pluralities of assay mixtures are run in parallel with different candidate composition concentrations to obtain a differential response to the various concentrations. Typically, one of these concentrations serves as a negative control, i.e. at zero concentration or below the level of detection.

Candidate compositions encompass numerous chemical classes, though typically they are organic molecules, preferably small organic compounds having a molecular weight of more than 50 and less than about 2,500 daltons. Candidate compositions comprise functional groups necessary for structural interaction with proteins, particularly hydrogen bonding, and typically include at least an amine, carbonyl, hydroxyl or carboxyl group, preferably at least two of the functional chemical groups. The candidate compositions often comprise cyclical carbon or heterocyclic structures and/or aromatic or polyaromatic structures substituted with one or more of the above functional groups. Candidate compositions are also found among biomolecules including, but not limited to: peptides, saccharides, fatty acids, steroids, purines, pyrimidines, derivatives, structural analogs or combinations thereof.

Candidate compositions are obtained from a wide variety of sources including libraries of synthetic or natural compounds. For example, numerous approaches are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical approaches, and can be used to produce combinatorial libraries. Known pharmacological agents can be subjected to directed or random chemical modifications, such as acylation, alkylation, esterification, amidification, etc. to produce structural analogs.

EXAMPLES

The following Examples have been included to illustrate representative embodiments of the presently disclosed subject matter. In light of the present disclosure and the general level of skill in the art, those of skill will appreciate that the following Examples are intended to be exemplary only and that numerous changes, modifications and alterations can be employed without departing from the spirit and scope of the presently disclosed subject matter.

Materials and Methods Employed in Examples

Materials and Methods
  Mouse Strains:
  A bigenic mouse was produced by crossing APPSwDI (Swedish K760N/M671L, Dutch E693Q and Iowa D694N) transgenic mice with $NOS2^{-/-}$ (B6 129P2NOS2$^{tau1Lau}$/J) mice (Jackson Laboratory, Bar Harbor, Me.). The phenotype of these individual mice has previously been reported (Davis et al., 2004; Laubach et al., 1995). All mice were genotyped by using standard PCR methods. APPSwDI transgenic mice were also bred to be used as age matched controls. For stereological counts we also used age-matched wildtype and $NOS2^{-/-}$ mice.
  Behavioral Analyses:
  APPSwDI (n=9) and APPSwDI/NOS2-/- (n=29) mice were tested at 52-56 weeks using both the two-day radial-arm water maze (Alamed et al., 2006) and the Barnes maze (Xu et al., 2007b). The two-day radial-arm water maze has been described in detail previously (Alamed et al., 2006). Briefly, a six arm maze is submerged in a pool of water and a platform is placed at the end of one arm. The mouse receives 15 trials per day for two days and on each trial is started in a different arm while the arm containing the platform remains the same for each mouse. Using visual cues around the room the mouse learns the position of the escape platform. The first 10 trials are considered training and alternate between a visible and a hidden platform. The final trials for day 1 and all trials on day 2 use a hidden platform. The number of errors are counted over a one minute period. The errors are averaged over three trials resulting in 10 blocks for the two day period.

The Barnes maze has also been described previously (Barnes, 1979) (Xu et al., 2007a). Briefly, this task was performed over a 5 day period and used a circular table with holes around the perimeter. An escape box was placed under an escape hole, the location of which remained constant over the five days for each mouse. Mice were tested twice daily for five days. The number of nose pokes was counted on each trial. The two trials on each day were averaged to provide one value per day.

Tissue Processing and Histological Methods:
  Mice were injected with a lethal dose of ketamine and perfused intracardially with 25 ml normal saline. Brains were rapidly removed and bisected in the mid-sagittal plane. One half was immersion fixed in either 70% ethanol (APPSwDI n=4 and APPSwDI/NOS2-/- n=4) or 4% paraformaldehyde (APPSwDI n=4 and APPSwDI/NOS2-/- n=8). One half was snap frozen in liquid nitrogen and stored at -80° C. The hemibrains fixed in 70% ethanol were embedded in paraffin and 8 µm sections were cut using a microtome. The hemibrains fixed in 4% paraformaldehyde were incubated for 24 h in 10, 20 and 30% sucrose sequentially to cryoprotect them. 25 µm frozen sagittal sections were then collected using a sliding microtome and were stored at 4° C. in PBS with sodium azide to prevent microbial growth. Eight equally spaced sections approximately 600 µm apart were selected for free floating immunohistochemistry for neuN (Mouse monoclonal, Chemicon, Temecula, Calif. 1:3000), PHF-tau (AT8, a mouse monoclonal for PHF-tau recognizing phosphorylated Ser202 in tau, Pierce Endogen, Rockford, Ill. 1:150), total tau (tau-5, mouse monoclonal anti-tau 5, Calbiochem, San Diego, Calif. 1:1000), cleaved caspase-3 (rabbit polyclonal, Cell Signaling Technology, Beverley, Mass. 1:300) or CD45 (rat monoclonal, AbD Serotec, Raleigh, N.C.). The method for free-floating immunohistochemistry has been described previously (Wilcock et al., 2004). Also, eight equally spaced sections were mounted on slides and stained with 1% thioflavine-S, 0.0001% FLUORO-JADE C™ in 0.1% acetic acid or TUNEL (using Dead-End Colorimetric TUNEL System, Promega, Madison, Wis.; stained according to manufacturer's instructions).

Four equally spaced sections spaced approximately 1.2 mm apart were taken from three mice of each genotype and mounted on slides. Double-immunofluorescence was performed for neuron specific β-tubulin (rabbit polyclonal, Abcam, Cambridge, Mass., 1:1000) and AT8. Appropriate alexa-fluor conjugated secondaries were used.

Aβ immunohistochemistry was performed on 70% ethanol fixed 8 µm paraffin-embedded sections. Briefly, sections were de-paraffined in xylene and rehydrated. Following incubations in hydrogen perxode and detergent, sections were incubated overnight at 4° C. with primary antibody (rabbit polyclonal anti-Aβ N terminal, Biosource, Camarillo, Calif. 1:3000). The sections were then incubated with biotinylated anti-rabbit secondary antibody (Vector Laboratories, Burlingame, Calif. 1:3000) for two hours at room temperature followed by incubation in streptavidin ABC (Vectastain elite ABC kit, Vector Laboratories, Burlingame, Calif.). The peroxidase was developed using a DAB substrate kit (Vector Laboratories, Burlingame, Calif.).

Quantification Methods:
  Images of the immunohistochemical stain were collected using the 20× objective lens on the Nikon ECLIPSE TE200™ microscope with a Nikon DXM1200™ digital camera attached. Images from the frontal cortex, CA1, CA3, dentate gyrus, subiculum and thalamus were collected from each section. An average of 4-5 sections for each animal were analyzed. Using the IMAGE-PRO PLUS™ software the positive stain was identified on several images and the red, green and blue values were saved to a file. This file was then applied to all images to yield measurements of percent area occupied with positive stain and average intensity of the positive stain for every image. Anatomical landmarks on the sections were used to ensure the same region was being taken on every section. Images for each marker were collected on the same day to ensure the same illumination on every image. The data was then exported to a spreadsheet where statistical analysis was performed.

Stereological Analysis:

Neurons stained positive for neuN were counted in the hippocampus, the cornu ammonis 3 (CA3) and the subiculum using the optical fractionator method of stereological counting (West et al., 1991) using a commercially available stereological software (STEREOINVESTIGATOR™). A systematic random sampling of sections throughout the left hippocampus were stained as described above and coded to ensure blinding. On each section, the regions of interests (ROI) were defined using specific landmarks within the hippocampus to maintain consistency. A grid was placed randomly over the ROI. At regularly predetermined positions of the grid, cells were counted within three-dimensional optical disectors. Within each disector, a 1 µm guard distance from the top and bottom of the section surface was excluded. Section thickness was measured regularly on all collected sections to estimate the mean section thickness for each animal after tissue processing and averaged 12.34 µm±0.32 µm for all sections analyzed. The total number of neurons was calculated using the equation:

$$N = Q^- \times 1/ssf \times 1/asf \times 1/hsf$$

where N is total neuron number, $Q^-$ is the number of neurons counted, ssf is section sampling fraction, asf is the area sampling fraction and hsf is the height sampling fraction.

Aβ ELISA:

Soluble and insoluble pools of Aβ1-40 and Aβ1-42 were measured by sandwich ELISA as previously described (Miao et al., 2005). Briefly, the snap frozen hemibrain was pulverized using a mortar and pestle on dry ice. Soluble Aβ pools were obtained using carbonate extraction. The pellet left over from this step was then homogenized with guanidine to yield the insoluble Aβ pool. Total Aβ1-40 and 1-42 levels were obtained by adding together the soluble and insoluble values.

Western Blotting:

Protein was extracted from pulverized brain powder and quantified using the BCA protein assay kit (Pierce Biotechnology Inc. Rockford, Ill. Performed according to manufacturer's instructions). 10 µg protein from each sample were run on a denaturing 4-20% SDS-PAGE gel. The gel was then transferred onto a nitrocellulose membrane. The transferred membrane was then blocked in 5% non-fat milk and incubated overnight at 4° C. in AT8 anti-PHF tau antibody (1:150) diluted in 5% non-fat milk. The following day the membrane was washed in TBST (tris buffered saline with 1% tween-20) and incubated for one hour in HRP conjugated anti-mouse secondary antibody (1:2000) dissolved in 5% non-fat milk. The membrane was then washed in TBST and developed using the ECL advance western blotting detection kit (GE Healthcare, Buckinghamshire, UK). Autoradiography film was exposed to the blot and developed. The blot was stripped using Restore stripping buffer (Pierce Biotechnology Inc, Rockford, Ill.). It was then reprobed using the above protocol for GAPDH (mouse anti-GAPDH, Advanced ImmunoChemical Inc., Long Beach, Calif., 1:10,000) to ensure accurate gel loading.

Statistics:

Behavior data was analyzed at each data point by one-way analysis of variance (ANOVA). The data was also analyzed to detect overall genotype difference by using the unpaired Student's t test. All immunohistochemical and ELISA data was analyzed by one-way ANOVA. The GraphPad Prism 4 program (GraphPad, San Diego, Calif.) was used to perform all statistical analyses.

Overview of Examples 1-4

Alzheimer's disease (AD) is a complex disorder characterized by three primary pathologies in the brain; amyloid plaques, neurofibrillary tangles and massive neuron loss. Mouse models have been extremely useful for studying individual components of the disease but have been limited in their ability to fully recapitulate all of these pathologies. Disclosed herein is the crossing of a APPSwDI transgenic mouse, which develops vascular and parenchymal amyloid β-protein (Aβ) deposits only, with a NOS2 knockout mouse. The APPSwDI/NOS2–/– mice displayed significantly impaired spatial memory compared to the APPSwDI parent, even though total Aβ levels were the same in both mice. APPSwDI mice do not show neuron loss or tau pathology while APPSwDI/NOS2–/– mice displayed significant reductions in hippocampal neuron numbers and extensive tau hyperphosphorylation, redistribution and aggregation. These data show that removal of NOS2 from an APP transgenic mouse results in development of full AD-like pathology and behavioral impairments.

Three pathologies should be present in the brain for a definitive diagnosis of Alzheimer's disease (AD): amyloid plaques composed of β-amyloid aggregates, neurofibrillary tangles composed of hyperphosphorylated and aggregated tau, and neuron loss. The amyloid hypothesis proposes that β-amyloid accumulation is toxic to the brain resulting in hyperphosphorylation of tau, neuronal death and cognitive deficits. Transgenic mouse models expressing mutant human APP successfully produce amyloid plaques and some cognitive decline, but lack significant neuron loss and any tau pathology. Transgenic mouse models expressing human tau with mutations associated with frontotemporal dementia display tau pathology, but they fail to show amyloid deposition. Transgenics expressing APP and TAU genes have been developed that display both amyloid plaques and tau aggregates. As presented in the Examples, Tg2576 APP transgenic mice crossed to a nitric oxide synthase 2 (NOS2) knockout (NOS2–/–) develop neurofibrillary tangle-like pathology from endogenous mouse tau and show evidence of neurodegeneration following staining for fluoro-jade C and activated caspase 3.

The NOS2 gene encodes inducible NOS (iNOS), one of three isoforms of NOS that generate nitric oxide (NO) in the body, and is primarily associated with the innate immune response in all tissues. While NO is commonly considered a "cytotoxic" molecule, which is its function during acute disease, NO is also pro-growth and anti-apoptotic. This apparent dichotomy of NO's functions, relates to an integration of its tissue concentration, its levels of production, and the wide variety of targets for NO and its metabolites (Wink). Shown herein is that the APPSwDI transgenic mouse crossed to a NOS2–/– mouse develops tau pathology, significant neuron loss in the brain and further cognitive decline in behavioral tests despite unaltering levels of Aβ.

NO is now known to be part of a broad "cellular defense response" and is likely to act at multiple intracellular sites. For example, NO regulates the electron transport chain (ETC) by inhibiting the mitochondrial cytochrome c oxidase (Complex 4 of the respiratory chain). This action promotes slowing of cellular oxygen utilization, conservation of oxygen for other (non mitochondrial) cellular processes, changes in mitochondrial calcium release and the subsequent activation of specific cell signaling pathways. Cho et al. have suggested that NO is essential to ischemic preconditioning by enhancing the resistance of mitochondria to injury. The upregulated genes in this process appear to be stress-responsive genes that can act in a cytoprotective manner. Other cytoprotective proteins such as hemoxygenase I (HO-1), Mn-SOD and Bcl-2 are up-regulated by reactive nitrogen species. Furthermore, NO is an effective anti-oxidant, preventing oxidative modification of proteins and lipids caused by other oxidizing species such as $H_2O_2$. Finally, NO can work thru NGF independent pathways to promote neuronal survival. Thus, maintenance of a critical NO level could be an adaptive response of cells in the brain to the chronic stress of the neurodegenerative disease process in AD. The lack of the pathological changes in NOS2 control mice clearly show that an additional stress such as Abeta must be present. In turn, the overall level depends on the balance between the supply of NO (regardless of the source) and the "removal" of NO by interaction with cellular constituents including oxidized lipids (which are abundant in the brain under stressful conditions such as AD).

Example 1

A bigenic mouse was produced by crossing APPSwDI (Swedish K760N/M671L, Dutch E693Q and Iowa D694N) transgenic mice with NOS2 knockout (NOS2-/-; B6 129P2NOS2$^{tm1Lau}$/J) mice (Jackson Laboratory, Bar Harbor, Me.). APPSwDI and APPSwDI/NOS2-/- mice were tested for spatial memory at 52-56 weeks of age. The two day radial-arm water maze task has previously been shown to detect spatial learning and memory deficits in APP transgenic mice. FIG. 1A shows that the APPSwDI/NOS2-/- mice make significantly more errors in the radial-arm water maze than do the APPSwDI mice (two-way ANOVA p<0.005). This difference is particularly apparent on day 2 when the APPSwDI mice are making less than 1 error, indicating acquisition and retrieval of the task, while the APPSwDI/NOS2-/- mice are still making 2 errors or more. Regression analysis of the slopes also showed significant differences (P<0.05) suggesting slowed or less rapid learning and/or retrieval of the task by the APPSwDI/NOS2-/- mice. The Barnes maze was also performed, another spatial memory test previously shown to detect deficits in APP transgenic mice. FIG. 1B shows that the APPSwDI/NOS2-/- mice are also significantly impaired in this task (two-way ANOVA p<0.05, slope difference P<0.001). The APPSwDI transgenic mice at this age have been shown to have demonstrable impairment in the Barnes maze and, thus, the removal of NOS2 results in further cognitive decline in these mice. This further decline is not due to increased amyloid production or deposition since no change in soluble or insoluble, Aβ40 or Aβ42 levels were observed (FIG. 1C).

Example 2

Figure 2:
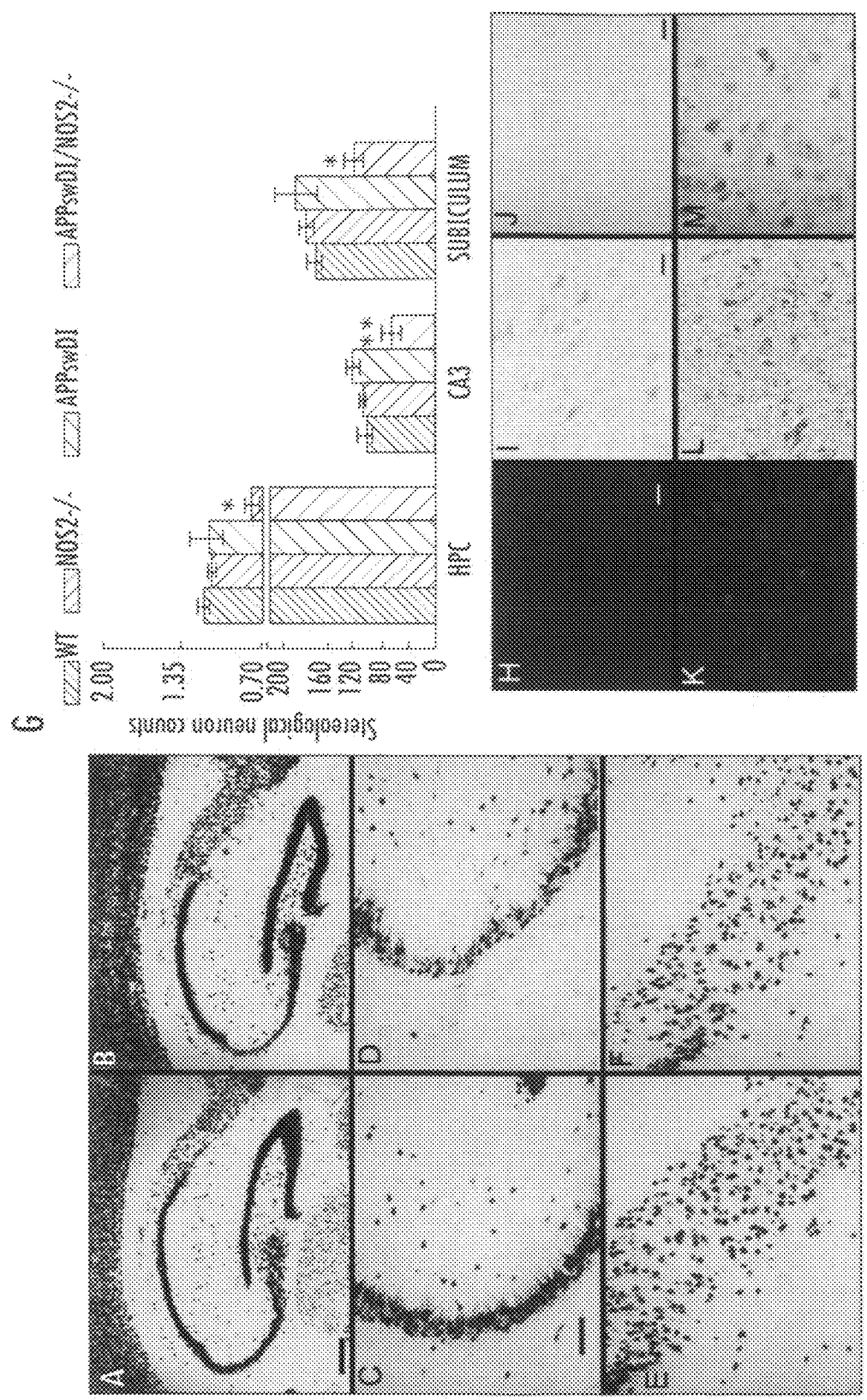
FIGS. 2A-2M show that significant neuron loss is observed in the APPSwDI/NOS2−/− mouse.

To determine if neuronal damage or loss could account for the significantly increased behavioral deficit in the APPSwDI/NOS2-/- mice compared to control APPSwDI mice, neuronal integrity in hippocampal regions was examined. Immunostaining for the neuronal marker, NeuN on equally spaced sagittal sections revealed thinning of the CA3 (FIGS. 2B and 2D) and subiculum (FIGS. 2B and 2F) in APPSwDI/NOS2-/- mice. Stereological counting of neurons was performed using the optical fractionator method in the entire hippocampus as well as the CA3 region and the neighboring subiculum (FIG. 2G). A 30% loss of neurons was found in the hippocampus (P<0.05 compared to wildtype, NOS2-/- or APPSwDI), a 35% loss of neurons in the subiculum (P<0.01 compared to wildtype, NOS2-/- or APPSwDI) and a 40% loss of neurons in the CA3 region of the hippocampus (P<0.01 compared to wildtype, NOS2-/- or APPSwDI).

FLUORO-JADE C™ stains degenerating neurons regardless of the cause of damage (Schmued). Numerous fluorojade C positive neurons were observed in the APPSwDI/NOS2-/- mice (FIG. 2K) compared to only background staining in the APPSwDI mice (FIG. 2H). Two markers of apoptosis were then examined to determine whether the neuronal death was due, at least in part, to apoptotic mechanisms. Caspase 3 cleavage is a critical step in the apoptotic pathway and has been associated with Aβ-mediated neuronal death. Immunocytochemistry for cleaved caspase 3 showed positive staining of the neurons in the APPSwDI/NOS2-/- mice (FIG. 2L). TUNEL is a staining technique used to detect fragmented nuclear DNA, which is indicative of apoptosis. Numerous TUNEL positive neurons were detected in the APPSwDI/NOS2-/- mice (FIG. 2M). Together, all of these data indicate that the APPSwDI/NOS2-/- has significant neurodegeneration that may primarily result from apoptotic mechanisms.

Example 3

Figure 3:
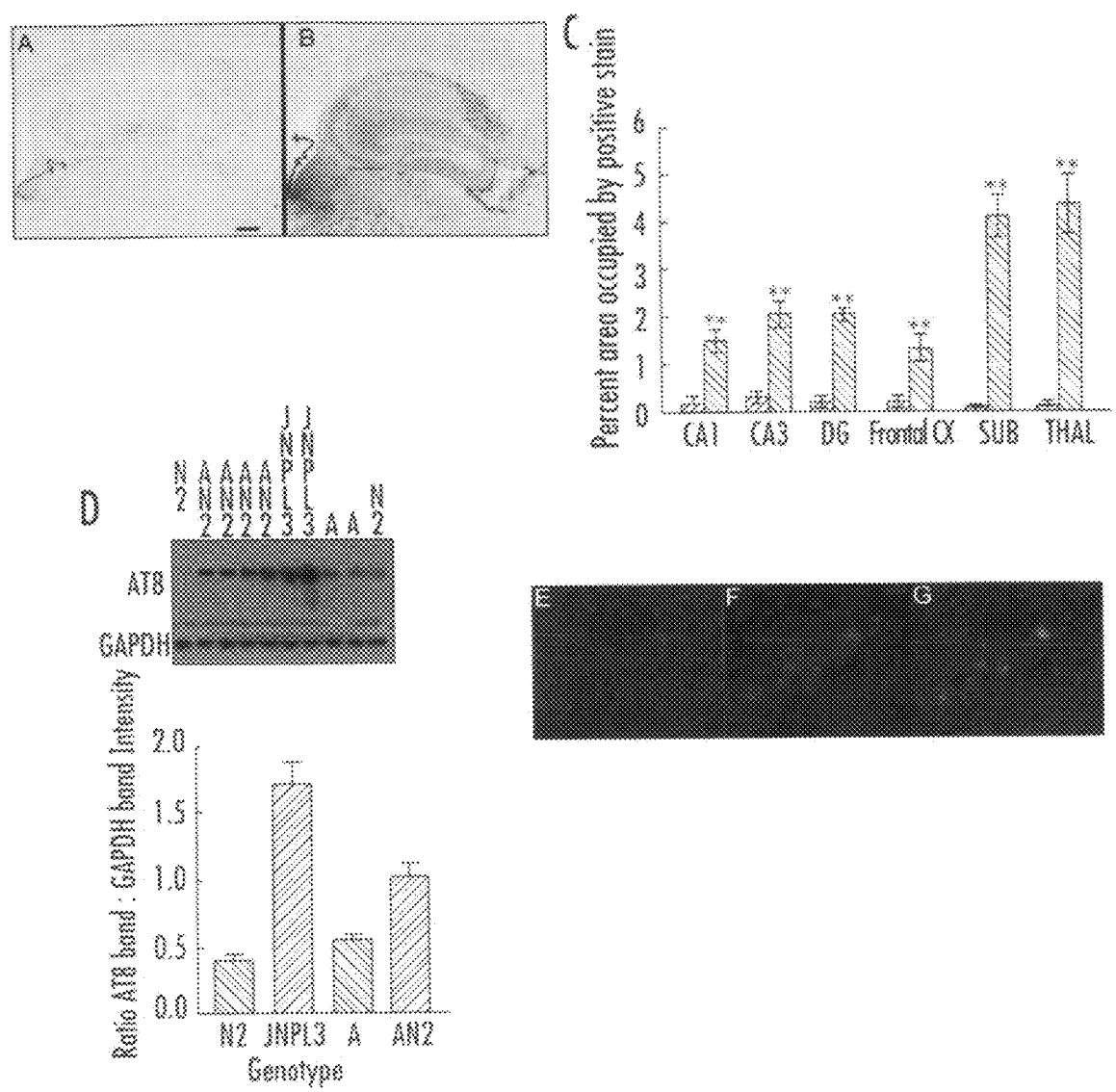
FIGS. 3A-3G show that tau hyperphosphorylation and redistribution is observed in APPSwDI/NOS2−/− mice. AT8 immunohistochemistry labels tau phosphorylated at ser202, which is a pathological phosphorylation site.

Tau hyperphosphorylation and aggregation has been linked to neuronal damage and loss in AD and is predicted to be a downstream effect of Aβ action. To determine if changes in normal mouse tau are a potential cause of the neuronal degeneration in the hippocampus of the APPSwDI/NOS2-/- mouse, the brains were examined for tau pathology. AT8 is a well-recognized antibody used to detect a pathologically relevant hyperphosphoryslated tau epitope that is common to both mouse and human tau. Immunocytochemistry for AT8 showed significant staining in the hippocampus of the APPSwDI/NOS2-/- mice (FIG. 3B) compared to the APPSwDI mice (FIG. 3A). The level of AT8 immunoreactivity was quantified by measuring the percent area occupied by positive stain and AT8 staining was significantly increased in all regions examined (CA1, CA3, dentate gyrus, frontal cortex, subiculum and thalamus, all P<0.01). To confirm the immunocytochemical findings, a western blot was also performed on brain lysates using AT8. Prominent immunoreactive bands were observed for lysates from APPSwDI/NOS2-/- mice and from mice expressing the human P301L mutation (JNPL3) that served as a positive control for hyperphosphorylated tau. Low amounts of AT8 immunoreactive bands were also observed for NOS2-/- mice and APPSwDI mice (FIG. 3D). However, densitometric analysis of the bands, normalized to GAPDH as a loading control, showed much greater density in the APPSwDI/NOS2-/- mice when compared with the parental NOS2--/- and the APPSwDI mice (FIG. 3D). To confirm that the AT8 staining was intraneuronal, double immunofluorescence labeling was performed on representative brain sections. Neuron specific β-tubulin was used to label all neurons (FIG. 3E) while AT8 labeled only hyperphosphorylated tau (FIG. 3F). A merged image of the two stains shows AT8 staining co-localized with neuron-specific β-tubulin in neuronal cell bodies (FIG. 3G).

Example 4

Figure 4:
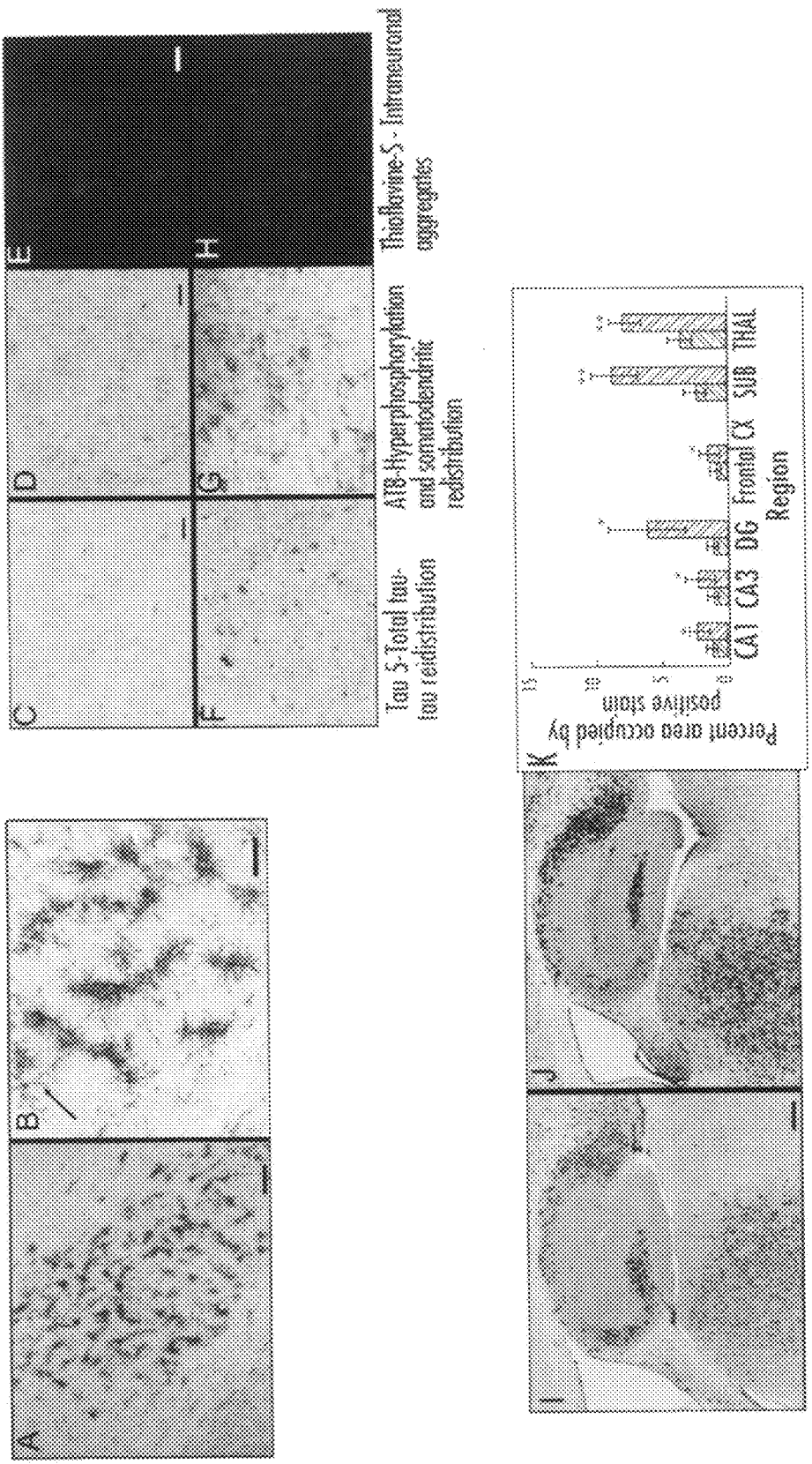
FIGS. 4A-4K show tau pathology and microglial activation is observed in the APPSwDI/NOS2−/−.

The Aβ deposition pattern in the APPSwDI shows extensive microvascular amyloid accumulation in the subiculum and thalamus in addition to microvascular and parenchymal Aβ accumulation in other brain regions. Interestingly, strong AT8 staining was found in perivascular processes in the subiculum (FIG. 4A) and thalamus, regions rich in microvascular amyloid. When examined at higher magnification, the AT8-positive processes appear to make direct contact with blood vessels. As indicated by the arrow in FIG. 4B, some of the AT8 immunoreactive cells demonstrate a branching morphology similar to interneurons; cells which are known to be a component of the neurovascular unit. While this staining pattern in the subiculum and thalamus was striking, significant somatodendritic staining was also observed in neurons from the APPSwDI/NOS2$^{-/-}$ mouse using the Tau 5 antibody that stains total tau (FIG. 4F). The redistribution of tau to the dendrites and soma is also indicative of pathological tau and was not observed in neurons from the parental APPSwDI mouse (FIG. 4C). Neuronal AT8 immunoreactivity located in the somatodendritic compartment was also observed in cortical regions in the APPSwDI/NOS2−/− mouse (FIG. 4G), but not in the APPSwDI mouse (FIG. 4D). Thioflavin-S, which is a fluorescent dye staining aggregated proteins in the β-pleated sheet conformation, labels only blood vessels in the APPSwDI mouse (FIG. 4E) and confirms the presence of compacted amyloid deposits in the microvasculature of this transgenic line. In the APPSwDI/NOS2−/− mouse, however, intraneuronal staining was also found for thioflavin-S demonstrating the presence of intraneuronal aggregates (FIG. 4H). Since intraneuronal Aβ staining was not observed in either mouse strain, and since AT8-positive tau is similarly found in the neuronal somatodendritic compartment, it is likely that the observed intraneuronal thioflavin-S staining in the APPSwDI/NOS2−/− mouse brain is produced by these tau aggregates. In addition to the neuron loss and tau pathology, increased microglial activation was also observed as determined by CD45 immunohistochemistry. Intense CD45 staining was seen throughout the hippocampus in the APPSwDI/NOS2−/− mouse brain (FIG. 4J), but was also found in the APPSwDI mouse (FIG. 4I). The increase in microglial activation in the subiculum and thalamus was particularly striking in the APPSwDI/NOS2−/− compared to the APPSwDI mouse, consistent with the strong perivascular tau pathology. Quantification of microglial activation by measuring percent area occupied by CD45 positive staining showed significantly increased activation in the APPSwDI/NOS2−/− compared to the APPSwDI mouse particularly for the thalamus and subiculum (FIG. 4K).

Discussion of Examples 1-4

Replication of AD-like pathology in mice by the sole accumulation of amyloid peptides leading to abnormal tau pathology, neuronal loss and cognitive dysfunction has proven to be elusive. Incomplete pathological models that show abundant amyloid deposition with little or sparse tau pathology, rare neuronal loss and limited changes in learning and memory behaviors have been most commonly generated. Disclosed herein is an approach to progress an amyloid depositing APP transgenic mouse to more complete Alzheimer's-like pathology with robust behavioral deficits. This is accomplished by genetically removing NOS2, and its iNOS protein product in mice that concomitantly express mutated human APP and deposit Aβ.

While it is not desired to be bound by any particular theory of operation, the presently disclosed data on the APPSwDI/NOS2−/− mouse and the study on the Tg2576 APP mouse on a NOS2 knockout background (see. Examples 5-10) add evidence suggesting that NO generated by iNOS under conditions of long-term injury or disease reduces functional loss and mitigates pathological changes in brain.

Unlike other mouse models of AD, the APPSwDI/NOS2−/− mouse shows a clear link between amyloid deposition; endogenous normal (not mutated) tau hyperphosphorylation, re-distribution and aggregation; neuronal loss; and cognitive behavioral changes. The APPSwDI/NOS2−/− mouse model also re-enforces a role for tau in Aβ-mediated pathology and behavioral deficits. Neuronal loss in the hippocampus was associated with Aβ deposits only when pathological tau was also observed. The combined presence of Aβ and pathological tau was also associated with significantly greater loss of learning and memory in the APPSwDI/NOS2−/− mouse. In contrast, an equivalent level of Aβ in the control APPSwDI mice, was associated with minimal behavioral impairment and supports the idea that Aβ affects neuronal function independently of tau pathology. However, progression to significant neuronal loss and significant behavioral deficits requires tau pathology, as we show in this case which is generated by the lack of iNOS and the accompanying loss of its enzymatic production of NO.

Methods Employed in Examples 5-10

Mouse Strains

A bigenic mouse was produced by crossing Tg (HuAPP695.K670NM671L)2576 mice with NOS2$^{-/-}$ (B6 129P2NOS2$^{tau1Lau}$/J) (Jackson Laboratory, Bar Harbor, Me.) mice. Phenotypes of APPsw and NOS2$^{-/-}$ mice have been described (Hsiao et al., (1996) *Science* 274, 99-102; Laubach et al., (1995) *Proc. Natl. Acad. Sci. USA* 92, 10688-10692). Tg2576 mice were a generous gift of K. Hsaio-Ashe (University of Minnesota, Minneapolis, Minn.). Littermate controls were generated from the backcrossed strain (≈75% C57BL/6 and 25% SJL/129 SVJ). JNPL3 (TAUP301L) mice were a generous gift from J. Lewis and M. Hutton (Mayo Clinic, Jacksonville, Fla.). All mice were genotyped by using standard procedures.

Immunocytochemistry Antibodies

Hyperphosphorylated tau was detected with the following antibodies: AT8-phospho-Ser-202/Thr-205 (1:500; Pierce Biotechnology, Rockford, Ill.), CP13-phospho-Ser-202/Thr-205 (1:600; a gift of Peter Davies, Albert Einstein College of Medicine, Bronx, N.Y.), and AT180-phosphor-Thr-231 (1:500; Pierce Biotechnology). Total phosphorylated and nonphosphorylated tau was detected with Tau5 (1:3,000; Calbiochem, San Diego, Calif.), and Aβ/amyloid deposits were detected with 4G8 (1:1,000; Senetek, Napa, Calif.). Activated caspase-3 was detected by using anti-active$^R$ caspase-3 (1:50; Cell Signaling Technology, Beverly, Mass.). Truncated tau was detected with TauC3 antibody [a generous gift of L. I. Binder (Northwestern University, Evanston, Ill.)].

Quantitative RT-PCR

Mouse brain RNA was extracted with the Versagene RNA Purification system (Gentra Systems, Minneapolis, Minn.) and converted to cDNA by using a High-Capacity cDNA archive kit (Applied Biosystems, Foster City, Calif.). NOS2 mRNA (GENBANK® Accession No. NM 010927) expression was identified with primer a (5'-GCATCCCAAGTAC- GAGTGGT-3'; SEQ ID NO: 1, spanning the exon 9/exon 10 boundary to ensure no amplification of genomic DNA) and primer b (5'-ATTCTGCCAGATGTGGGTCTTCCA-3'; SEQ ID NO: 2).

NOS Activity

NOS enzyme activity was measured by the conversion of L-arginine to L-citrulline as described (Weinberg et al., (1995) *Blood* 86, 1184-1195) and expressed as pmol of L-$^{14}$C-citrulline produced per mg of protein.

Aggregate Filter Assay

Aggregate levels were measured with a filter retardation assay (Heiser et al., (2002) *Proc. Natl. Acad. Sci. USA* 99, 16400-16406) and immunodetection for either total tau (Tau5) or hyperphosphorylated tau (AT8).

Scanning EM

Brain aggregates retained on filters as described were immunostained with Tau5 antibody and detected with goat antimouse IgG conjugated with 40 nM gold particles (1:20; Ted Pella, Redding, Calif.) and a silver enhancing kit (Ted Pella). A Phillips KL 30 environmental scanning electron microscope at the Duke Biological Science Environmental Scanning Electron Microscope facility was used for imaging with the kind assistance of Leslie Eibest.

Detection of Soluble and Insoluble A

Soluble and insoluble pools of Aβ40 and Aβ42 were measured with a specific ELISA and differential brain extractions as described (Miao et al., (2005) *J. Neurosci.* 25, 6271-6627; Schmidt et al., (2005) *Methods Mol. Biol.* 299, 279-298).

Statistics

Average values ±SEM were calculated for quantitative PCR and ELISA data (n=3-7 animals per group). Statistical significance was calculated by using the unpaired Student's t test with the Prism 3.02 program (GraphPad, San Diego, Calif.).

Overview of Examples 5-10

Alzheimer's disease is characterized by two primary pathological features: amyloid plaques and neurofibrillary tangles. The interconnection between amyloid and tau aggregates is of intense interest, but mouse models have yet to reveal a direct interrelationship. Shown herein is that NO is a factor that connects amyloid and tau pathologies. Genetic removal of NO synthase 2 in mice expressing mutated amyloid precursor protein results in pathological hyperphosphorylation of mouse tau, its redistribution to the somatodendritic compartment in cortical and hippocampal neurons, and aggregate formation. Lack of NO synthase 2 in the amyloid precursor protein Swedish mutant mouse increased insoluble β-amyloid peptide levels, neuronal degeneration, caspase-3 activation, and tau cleavage, suggesting that NO acts at a junction point between β-amyloid peptides, caspase activation, and tau aggregation.

Also disclosed herein is the induction of somatodendritic tau pathology in cortical and hippocampal neurons in a mouse model of AD that expresses the Swedish familial AD double mutation K670NM671L in APP (Tg2576) and that lacks a functional NO synthase (NOS) 2 gene. The NOS2 gene encodes inducible NOS (iNOS), one of three NOS protein isoforms (iNOS, neuronal NOS, and endothelial NOS) that produce NO in the brain. The presently disclosed data demonstrating hyperphosphorylation of tau at disease-specific sites, redistribution of tau to the somatodendritic compartment of cortical and hippocampal neurons, and tau aggregates in brains of mice expressing the APP Swedish mutation (APPsw) on a NOS2 knockout background strongly indicates NO to be protective in AD.

Example 5

Figure 5:
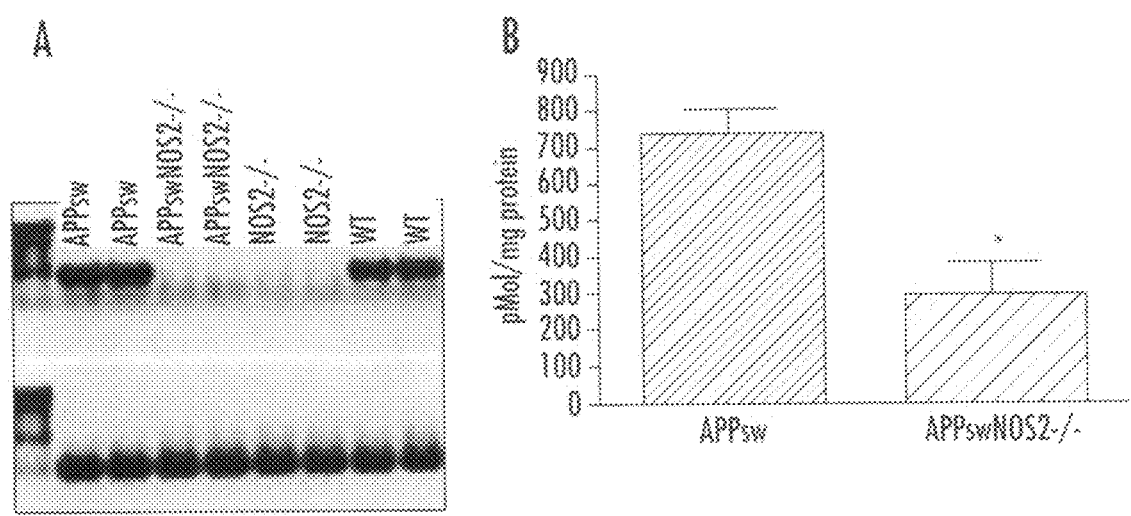
FIGS. 5A and 5B are an image and bar graph, respectively, showing loss of NOS2 RNA and activity. Brains from APPsw/NOS2−/− mice were assayed for the expression of NOS2 mRNA (FIG. 5A) and calciumindependent NOS activity (FIG. 5B). Detection of GAPDH mRNA served as a loading control in A. *, P=0.05.

Mice expressing APPsw on a NOS2 null background were assessed for the presence of NOS2 mRNA and brain NOS activity. mRNA for NOS2 was observed in WT and APPsw control littermates, but was not found in APPsw/NOS2$^{-/-}$ or NOS2$^{-/-}$ brains (FIG. 5A). To determine whether NOS activity fell when NOS2 was deleted in APPsw/NOS2$^{-/-}$ mice, calciumindependent NOS activity was measured in brain lysates from APPsw/NOS2$^{-/-}$ and APPsw mice by using the arginine-tocitrulline conversion assay. A significant decrease in activity was observed in the APPsw/NOS2$^{-/-}$ lysates compared with APPsw alone (FIG. 5B), indicating that NOS activity and, most likely, NO production was reduced in the bigenic mouse. Quantitative RT-PCR was used to detect compensatory changes in NOS1 and NOS3. NOS1 mRNA fell by 0.64±0.03-fold (n=5), whereas NOS3 mRNA increased by 1.48±0.13-fold (n=5) compared with WT littermates. These changes closely mimicked values observed in the NOS2$^{-/-}$ mouse (0.63±0.04 for NOS1 and 1.52±0.23 for NOS3). These data demonstrate that the compensatory changes in NOS1 and NOS3 are characteristic of the NOS2$^{-/-}$ deletion.

Example 6

The presence of abnormally phosphorylated tau was detected in APPsw/NOS2$^{-/-}$ mice (n=5) by using immunocytochemistry on brain sections with AT8, CP13, and AT180 antibodies to specific, disease-associated phosphorylation sites in tau protein (Weaver et al., (2000) *Neurobiol. Aging* 21, 719-727; Duff et al., (2000) *Neurobiol. Dis.* 7, 87-98; Goedert et al., (1995) *Neurosci. Lett.* 189, 167-169). Immunopositive staining for hyperphosphorylated tau was observed in the somatodendritic compartments of numerous neurons in the hippocampus (FIGS. 6A and 6F), globus pallidus (FIG. 6B), and frontal cortex (FIG. 6C) in APPsw/NOS2$^{-/-}$ brain. Both AT8 and CP13 produced similar patterns of staining in APPsw/NOS2$^{-/-}$ mice, whereas AT8/CP13 immunostaining was not observed in cortical sections frommNOS2$^{-/-}$ littermates (FIG. 6D) or hippocampal sections from APPsw littermates (FIG. 6E). Immunopositive phospho-tau was also seen in apical dendrites, and intracellular aggregate-like structures were observed in some neurons from the APPsw/NOS2$^{-/-}$ brains (FIG. 6B, arrows).

Figure 6:
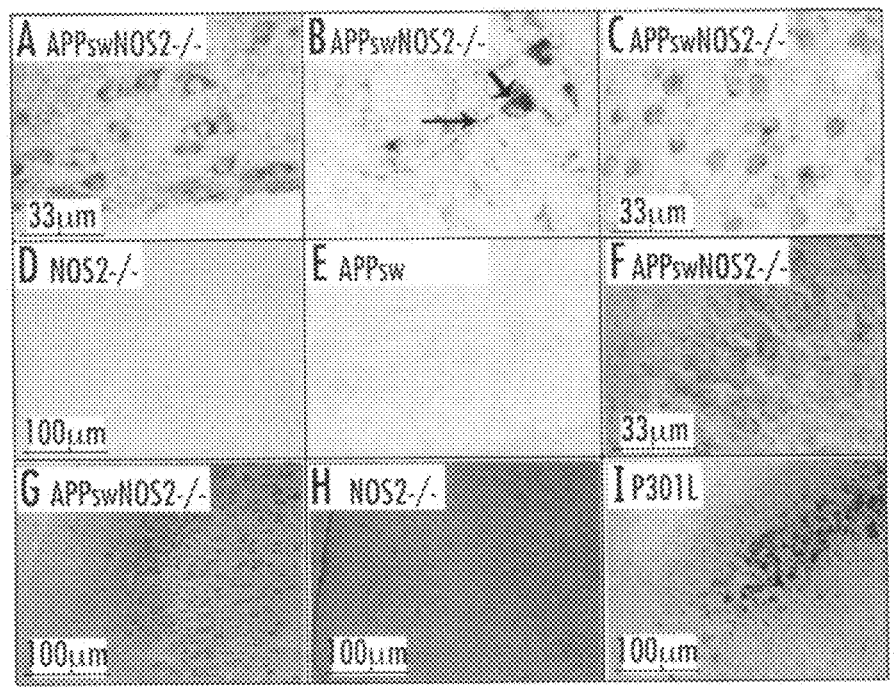
FIGS. 6A-6I show that the APPsw/NOS2−/− mouse demonstrates somatodendritic localization of hyperphosphorylated tau.

A similar immunostaining pattern was observed in brain sections with the AT180 antibody to phosphorylated Ser-231 (FIGS. 6G-6I). Phospho-tau immunoreactivity was again observed in the cell somas and apical dendrites of cortical and hippocampal neurons. The neuronal pattern of immunostaining in APPsw/NOS2$^{-/-}$ brains qualitatively resembled the AT180 immunostaining pattern observed in JNPL3 mice with the P301L human tau mutation (FIG. 6I) that express hyperphosphorylated and aggregated tau (Lewis et al., (2000) *Nat. Genet.* 25, 402-405).

Example 7

Figure 7:
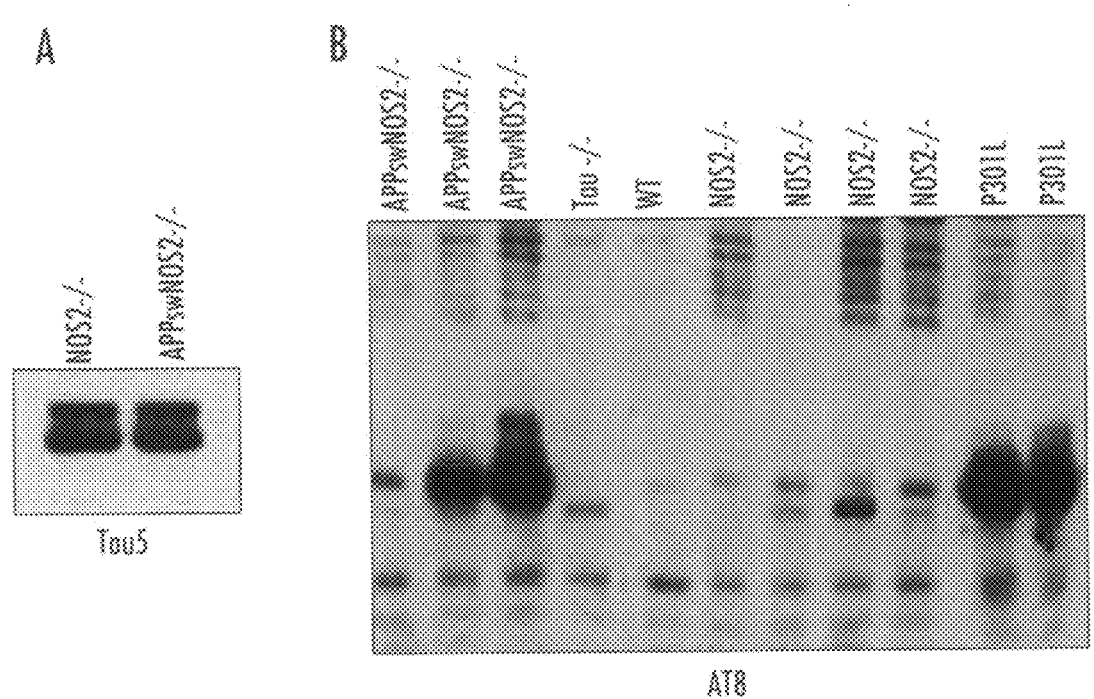
FIGS. 7A and 7B are images showing that western blot confirms the presence of hyperphosphorylated tau in APPsw/NOS2−/− brains.

To determine whether tau protein levels were altered in the APPsw/NOS2$^{-/-}$ mice, total tau expression was compared by using Western blots and the Tau5 antibody that detects both phosphorylated and nonphosphorylated forms of tau. No difference in total tau was observed between lysates from APPsw/NOS2$^{-/-}$ and NOS2$^{-/-}$ brains (FIG. 7A). Using the AT8 antibody, brain lysates were examined for the presence of hyperphosphorylated tau (FIG. 7B). Neither WT nor tau knockout mice demonstrated bands corresponding to hyperphosphorylated tau. In contrast, each of three individual APPsw/NOS2$^{-/-}$ brain samples demonstrated AT8 immunoreactivity. Interestingly, low levels of AT8-positive tau were seen in brain lysates from the NOS2$^{-/-}$ littermate controls.

Example 8

Figure 8:
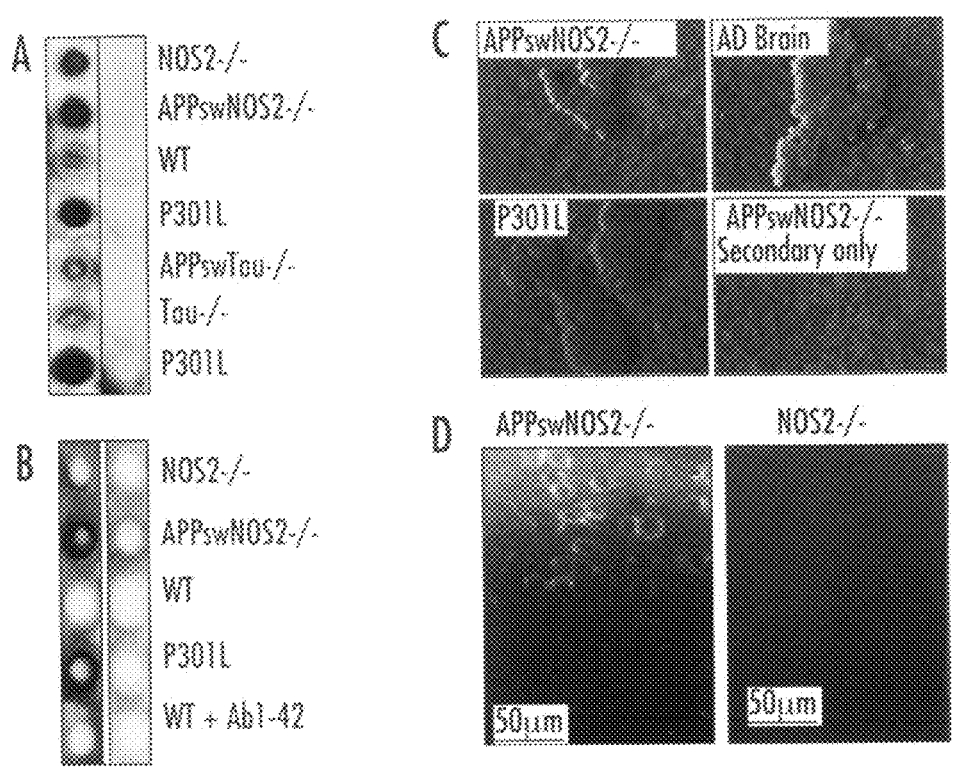
FIGS. 8A-8D are images showing that aggregated tau proteins are observed in APPsw/NOS2−/− brain.

To confirm the presence of aggregated tau, a filter assay was used (Heiser et al., (2002) *Proc. Natl. Acad. Sci. USA* 99, 16400-16406) that traps protein aggregates present in brain lysates on a cellulose filter. Tau5+ staining of trapped aggregates was observed with brain filtrates from NOS2$^{-/-}$, APPsw/NOS2$^{-/-}$, and P301L mice, whereas no staining was observed with brain filtrates from WT or tau$^{-/-}$ mice (FIG. 8A). AT8-immunoreactive hyperphosphorylated tau was found in filter-trapped aggregates from APPsw/NOS2$^{-/-}$ and P301L brains, with only slight immunoreactivity observed from the NOS2$^{-/-}$ filtrate (FIG. 8B).

Tau aggregation was further confirmed with scanning EM and thioflavin S histochemistry. Filters containing trapped tau aggregates were immunoreacted with Tau5 antibody, followed by an immunogold secondary antibody and silver enhancement to improve detection. Tau aggregates were clearly observed in brain filtrates from APPsw/NOS2$^{-/-}$ mice (FIG. 8C) and were comparable to immunoreactive tau aggregates prepared from brains of human AD or JNPL3 mice. Thioflavin S-positive aggregates were observed within the cell bodies of cortical neurons in the APPsw/NOS2$^{-/-}$ mice, but were not observed in NOS2$^{-/-}$ liftermates (FIG. 8D).

Example 9

Figure 9:
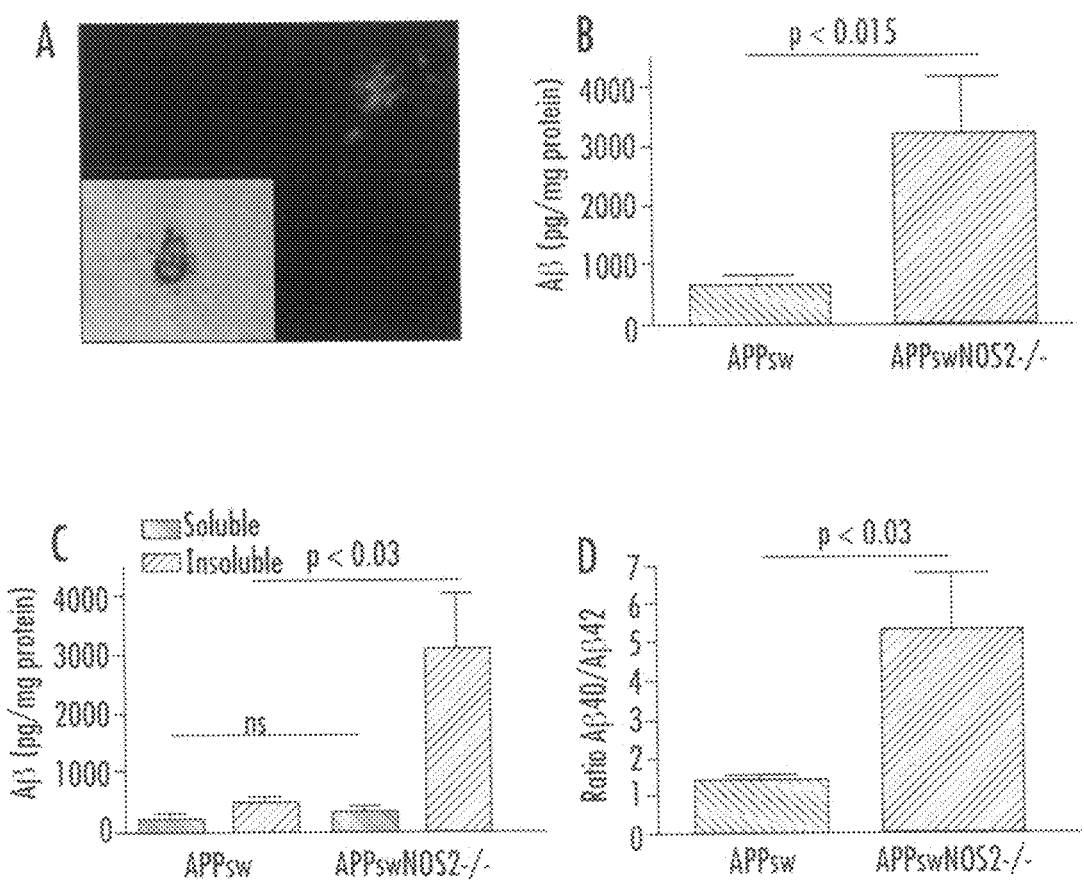
FIGS. 9A-9D are an image and bar graphs, respectively, showing total and insoluble Aβ is increased in the APPsw/NOS2−/− brain.
Figure 10:
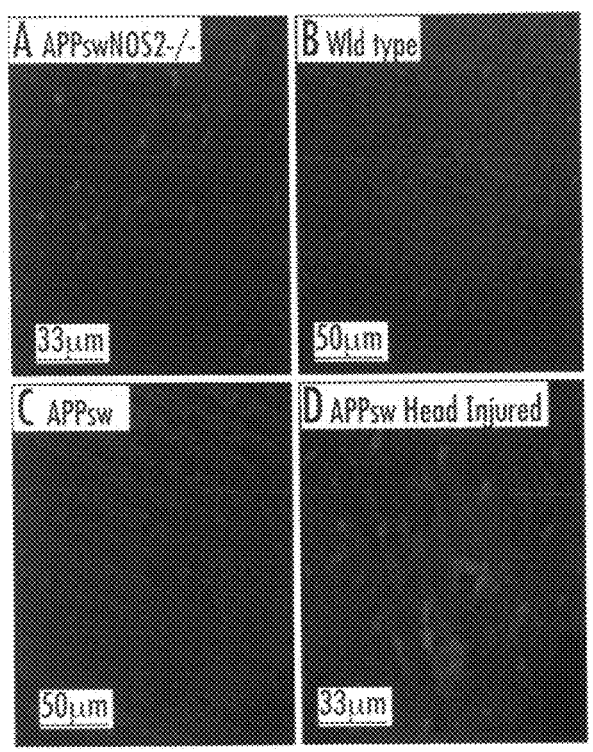
FIGS. 10A-10D are images showing that degenerating neurons are observed in the APPsw/NOS2−/− brain. FLUOROJADE B™ the reagent was used to detect degenerating neurons as described by Schmued et al. (Schmued et al., (2005) Brain Res. 1035, 24-31).

In addition to tau pathology, amyloid plaque-like pathology was observed in APPsw/NOS2$^{-/-}$ brains. Amyloid deposits could be detected by using 4G8, an antibody that reacts with human β-amyloid (Aβ) peptides, or thioflavin S, a fluorescent indicator for β-pleated sheet structures (FIG. 9A). To compare APPsw/NOS2$^{-/-}$ with APPsw liftermates, soluble and insoluble Aβ40 and Aβ42 levels were directly measured in brain lysates by using a quantitative ELISA (Miao et al., (2005) *J. Neurosci.* 25, 6271-6627; Schmidt et al., (2005) *Methods Mol. Biol.* 299, 279-298). Total brain Aβ levels were significantly greater in APPsw/NOS2$^{-/-}$ mice compared with APPsw littermate controls (FIG. 9B). This increase was caused by a significant increase in insoluble Aβ peptides, resulting in an increased Aβ40/Aβ42 ratio (FIGS. 9C and 9D). Although neuronal loss is not common in APPsw mice, FLUOROJADE B™ was used to identify degenerating neurons in the APPsw/NOS2$^{-/-}$ brains (Schmued et al., (2005) *Brain Res.* 1035, 24-31). Widespread cortical neuronal damage was observed in three of four APPsw/NOS2$^{-/-}$ mice compared with no apparent damage in either APPsw or WT brains (FIGS. 10A-10D). Head-injured APPsw mice served as a positive control and displayed numerous degenerating neurons.

Example 10

Figure 11:
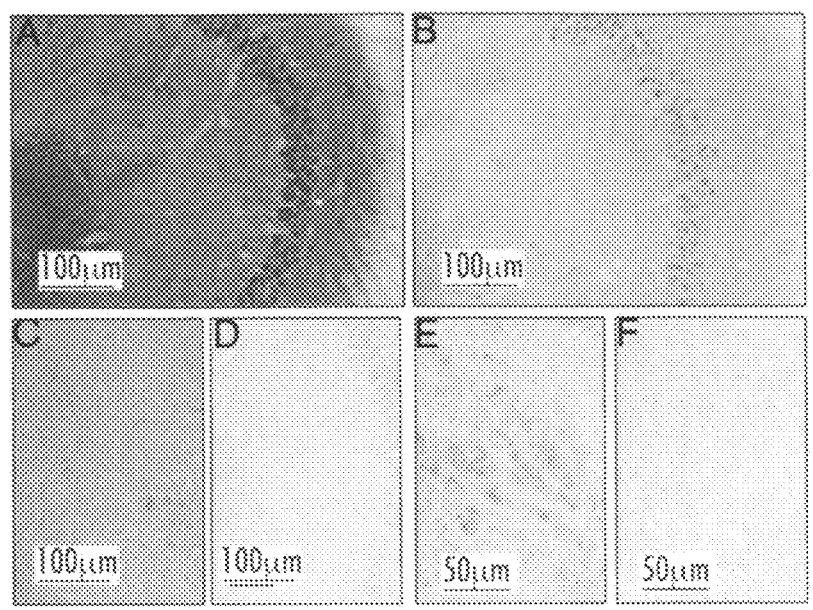
FIGS. 11A-11F are images showing that immunoreactivity for cleaved caspase-3 is increased in APPsw/NOS2−/− brain.

The mechanism of cell injury was further explored by evaluating markers for apoptosis. The activated form of caspase-3, a known executioner caspase involved in apoptotic cell death (Friedlander et al., (2003) *N. Engl. J. Med.* 348, 1365-1375), was detected by using immunocytochemistry. Activated caspase-3 was observed in cell bodies and apical dendrites in cortical and hippocampal neurons in APPsw/NOS2$^{-/-}$ brains (FIG. 11A). Slight, but observable, activated caspase-3 immunoreactivity was found in NOS2$^{-/-}$ brains versus background staining in APPsw or WT liftermates. To detect whether activated caspase cleaved tau, APPsw/NOS2$^{-/-}$ brain sections were immunostained with an antibody that recognizes tau truncated at Asp-421 (TauC3) (Gamblin et al., (2003) *Proc. Natl. Acad. Sci. USA* 100, 10032-10037). TauC3-positive staining was observed in cell bodies and dendrites of cortical neurons in APPsw/NOS2$^{-/-}$ mice (FIG. 11E) compared with APPsw control brains (FIG. 11F).

Discussion of Examples 5-10

The amyloid and tau pathologies that characterize AD brain lesions were simultaneously observed in the APPsw/NOS2$^{-/-}$ mouse brain. Unlike other common mouse models for amyloid deposition, redistribution of normal mouse tau to the somatodendritic region of cortical and hippocampal neurons, hyperphosphorylation of mouse tau at multiple, disease-associated residues, and mouse tau aggregates were observed. These changes occurred in the presence of nonmutated mouse tau and were associated with neuronal degeneration in the cortex. Amyloid plaque morphology and distribution in the APPsw/NOS2$^{-/-}$ brain was visually similar to that observed in APPsw littermates. However, a significant increase was observed in total brain Aβ peptides, which were primarily in the insoluble form. Increased levels of total Aβ peptides and altered ratios of Aβ40 to Aβ42 in the APPsw/NOS2$^{-/-}$ brain suggest that NO acts on Aβ generation or clearance, although it is not desired to be bound by any particular mechanism of interaction.

The presently disclosed data suggest that maintenance of a critical level of NO at the neuron plays a role in the survival programs that depend on NO signaling pathways. The source of NO might not be as important as the actual level of NO. In fact, changes in both NOS enzymes and NO scavengers were observed in AD. The presently disclosed quantitative PCR data support the idea that changes in constitutive NOS isoforms are unlikely to adequately compensate for the genetic loss of iNOS.

In summary, APPsw/NOS2$^{-/-}$ mice provide clear genetic data that removal of a major synthetic source of NO over a lifetime of exposure to Aβ peptides promotes tau pathology in the brain. Although it is not desired to be bound by any particular theory of operation, the presently disclosed data also suggest that Aβ, in the presence of reduced NO, could play a role in the production of hyperphosphorylated and aggregated tau, thereby regulating the merger of the two pathologies into the amyloid cascade hypothesis of Selkoe and coworkers (Selkoe et al., (2003) *Annu. Rev. Pharmacol. Toxicol.* 43, 545-584; Hardy et al., (2002) *Science* 297, 353-356). The potential for NO to act as an inhibitory modulator of caspase activity places NO at a junction point between Aβ peptides, caspase cleavage of tau, and tau aggregation. At the least, the APPsw/NOS2$^{-/-}$ mouse provides a tool to further understanding of the role of NO-mediated events in AD.

It will be understood that various details of the presently disclosed subject matter can be changed without departing from the scope of the presently disclosed subject matter. Furthermore, the foregoing description is for the purpose of illustration only, and not for the purpose of limitation.

What is claimed is:

1. A modified mouse comprising both:
(i) a transgene encoding a biologically active human Amyloid Peptide Precursor (APP) polypeptide comprising a Swedish familial K670N/M671L double mutation (APPsw), wherein the transgene encoding the biologically active human APP polypeptide comprising a Swedish familial K670N/M671L double mutation (APPsw) is integrated into the genome of the modified mouse under control of a promoter sequence; and
(ii) a knockout or knockdown of an inducible Nitric Oxide Synthase (iNOS) protein biological activity, wherein the knockout or knock-down of the iNOS protein biological activity comprises a genetic deletion of at least a subsequence of one or both endogenous NOS2 genes sufficient to decrease expression of the endogenous NOS2 gene, a NOS2 polypeptide encoded thereby, or both,
and further wherein the brain of the modified mouse exhibits tau hyperphosphorylation relative to the brain of a mouse that comprises the transgene but that lacks the knockout or knockdown of the iNOS protein biological activity.

2. The modified mouse of claim 1, wherein the knockout or knock-down of the iNOS protein biological activity reduces expression of iNOS protein in the brain of the modified mouse.

3. A method of testing a candidate composition for activity in the treatment of Alzheimer's Disease, the method comprising:
(a) providing a modified mouse that comprises both:
(i) a transgene encoding a biologically active human Amyloid Peptide Precursor (APP) polypeptide comprising a Swedish familial K670N/M671L double mutation (APPsw), wherein the transgene encoding the biologically active human APP polypeptide comprising a Swedish familial K670N/M671L double mutation (APPsw) is integrated into the genome of the modified mouse under control of a promoter sequence; and
(ii) a knockout or knockdown of an inducible Nitric Oxide Synthase (iNOS) protein biological activity, wherein the knockout or knock-down of the iNOS protein biological activity comprises a genetic deletion of at least a subsequence of one or both endogenous NOS2 genes sufficient to decrease expression of the endogenous NOS2 gene, a NOS2 polypeptide encoded thereby, or both,
wherein the brain of the modified mouse exhibits tau hyperphosphorylation relative to the brain of a mouse that comprises the transgene but that lacks the knockout or knockdown of the iNOS protein biological activity;
(b) administering the candidate composition to the modified mouse; and
(c) observing the modified mouse for determination of an ameliorating change in the modified mouse indicative of the activity of the candidate composition in the treatment of Alzheimer's Disease.

4. The modified mouse of claim 1, wherein the transgene encoding the biologically active human APP polypeptide comprising the Swedish familial K670N/M671L double mutation (APPsw) further comprises Dutch E693Q and Iowa D694N mutations (APPSwDI).

5. The modified mouse of claim 1, wherein the tau hyperphosphorylation in the brain of the modified mouse is detectable by binding of an AT8 antibody to a brain section from the modified mouse.

6. The modified mouse of claim 5, wherein the binding of the AT8 antibody to the brain section of the modified mouse is significantly higher to $P<0.05$ as compared to binding of the AT8 antibody to a section of a brain of a transgenic mouse comprising an APPSwDI transgene but lacking an iNOS knockout or knock-down.

7. The modified mouse of claim 6, wherein the binding of the AT8 antibody to the brain section of the modified mouse is significantly higher to $P<0.01$ in at least one brain region selected from the group consisting of frontal cortex, CA1, CA3, dentate gyrus, subiculum, and thalamus as compared to binding of the AT8 antibody to the same brain region of a transgenic mouse that comprises an APPSwDI transgene but lacks an iNOS knockout or knock-down.

8. The modified mouse of claim 1, wherein the knockout or knock-down of the iNOS protein biological activity comprises a genetic deletion of both endogenous NOS2 alleles.

9. The method of claim 3, wherein the knockout or knock-down of the iNOS protein biological activity reduces expression of iNOS protein in the brain of the modified mouse.

10. The method of claim 3, wherein the transgene encoding the biologically active human APP polypeptide comprising the Swedish familial K670N/M671L double mutation (APPsw) further comprises Dutch E693Q and Iowa D694N mutations (APPSwDI).

11. The method of claim 3, wherein tau hyperphosphorylation in the brain of the modified mouse is detectable by binding of an AT8 antibody to a brain section from the modified mouse.

12. The method of claim 11, wherein the binding of the AT8 antibody to the brain section of the modified mouse is significantly higher to $P<0.05$ as compared to binding of the AT8 antibody to a section of a brain of a transgenic mouse comprising an APPSwDI transgene but lacking an iNOS knockout or knock-down.

13. The method of claim 12, wherein the binding of the AT8 antibody to the brain section of the modified mouse is significantly higher to $P<0.01$ in at least one brain region selected from the group consisting of frontal cortex, CA1, CA3, dentate gyrus, subiculum, and thalamus as compared to binding of the AT8 antibody to the same brain region of a transgenic mouse that comprises an APPSwDI transgene but lacks an iNOS knockout or knock-down.

14. The method of claim 3, wherein the knockout or knock-down of the iNOS protein biological activity comprises a genetic deletion of both endogenous NOS2 alleles of the modified mouse.

* * * * *